United States Patent [19]
Kellogg et al.

[11] Patent Number: 5,929,302
[45] Date of Patent: *Jul. 27, 1999

[54] PLANT TISSUE/STAGE SPECIFIC PROMOTERS FOR REGULATED EXPRESSION OF TRANSGENES IN PLANTS

[76] Inventors: Jill Anne Kellogg; Richard Keith Bestwick, both of 6680 SW. Canby, Portland, Oreg. 97223

[ * ] Notice: This patent is subject to a terminal disclaimer.

[21] Appl. No.: 09/111,573

[22] Filed: Jul. 8, 1998

Related U.S. Application Data

[62] Division of application No. 08/592,936, Jan. 29, 1996, Pat. No. 5,783,393.

[51] Int. Cl.$^6$ .............................. A01H 1/06; A01H 5/00; C12P 21/00; C07H 21/04
[52] U.S. Cl. ........................ 800/278; 800/298; 435/419; 435/468; 536/24.1
[58] Field of Search .................................. 435/69.4, 419, 435/468; 536/24.1; 800/205, 250

[56] References Cited

FOREIGN PATENT DOCUMENTS

WO 93/11241  6/1993  WIPO.
WO 95/35387  12/1995  WIPO.
WO 95/35388  12/1995  WIPO.

OTHER PUBLICATIONS

Cordes et al., "Interaction of a developmentally regulated DNA–binding factor with sites flanking two different fruit–ripening genes from tomato," The Plant Cell 1:1025–1034 (1989).

Good, X., et al., "Reduced Ethylene Synthesis by Transgenic Tomatoes Expressing S–Adenosylmethionine Hydrolase," *Plant Mol. Biol.* 26:781–790 (1994).

Grellet, F., et al., "*A. thanliana* mRNA for Major Latex Protein Type 1," EMBL Sequence Database, Rel. 46, Accession No. X91960 (Dec. 6, 1995).

Klee, et al., "Control of ethylene synthesis by expression of a bacterial enzyme in transgenic tomato plants," The Plant Cell 3:1187–1193 (1991).

Oeller, et al., "Reversible inhibition of tomato fruit senescence by antisense RNA," Science 254:437–439 (1991).

Pozueta–Romero, J., et al., "Characterization of a Family of Genes Encoding a Fruit–Specific Wound–Stimulated Protein of Bell Pepper (*Capsicum annuum*): Identification of a New Family of Transposable Elements," *Plant Mol. Biol.* 28:1011–1025 (1995).

Williamson, B., et al., "A Polygalacturonase Inhibitor from Immature Raspberry Fruits: a Possible New Approach to Grey Mould Control," *Acta Horticul.* 352:601 (1993).

*Primary Examiner*—James Ketter
*Assistant Examiner*—William Sandals

[57] ABSTRACT

The present invention relates to chimeric genes having (i) a DNA sequence encoding a product of interest, and (ii) a dru1 promoter, where said DNA sequence is heterologous to said promoter and said DNA sequence is operably linked to said promoter to enable expression of said product. The invention describes vectors, cells, plants, and fruits carrying the chimeric gene, as well as methods related thereto.

16 Claims, 10 Drawing Sheets

```
>Nsi_I
|     .   10     .   20     .   30     .   40     .   50     .   60     .   70     .   80
|     *    *     *    *     *    *     *    *     *    *     *    *     *    *     *    *
ATGCATATCA ACAACTACGA ATAAAGAGAT CAGCCTTTCC GTATCTGGTG GATGTTTGAG TCGGTGATGA CCATCTAATT
      .   90     .  100     .  110     .  120     .  130     .  140     .  150     .  160
      *    *     *    *     *    *     *    *     *    *     *    *     *    *     *    *
AAAGAAAGAA GAAAAATTAT ACATATTGTG GACCTCCCCA TATATAATTC TTATCATCTT TGTTACTGCC ATTATGATTA
      .  170     .  180     .  190     .  200     .  210     .  220     .  230     .  240
      *    *     *    *     *    *     *    *     *    *     *    *     *    *     *    *
TAAAATGATA TTAAAGGGAT GGTGTACCGT GTACTAATCA AATATCTACC TGATCTTATT GATTTGAAAG ATCATAAAAA
      .  250     .  260     .  270     .  280     .  290     .  300     .  310     .  320
      *    *     *    *     *    *     *    *     *    *     *    *     *    *     *    *
GAAATTAAAA TTGTTCAAAA TAAACCCCTA GAATTATATA TAGTTCATTA AGTTCAAATT AATTCGTTTG AAACGTGTTA
      .  330     .  340     .  350     .  360     .  370     .  380     .  390     .  400
      *    *     *    *     *    *     *    *     *    *     *    *     *    *     *    *
AGCAACCCTA CAACGTACTA AGCACCCTAG CTCCCTTTGC CTCTCGGCGG TAAGAGGAGA TATCCTCAGT CGAATTATGA
      .  410     .  420     .  430     .  440     .  450     .  460     .  470     .  480
      *    *     *    *     *    *     *    *     *    *     *    *     *    *     *    *
GCCGATCGAG GAAAGCTCGA TCAGTTGGAA AATCTTTCTT TCTTATGGCC AAGTTGTTTC AAACAATATA TTGAATTATT
      .  490     .  500     .  510     .  520     .  530     .  540     .  550     .  560
      *    *     *    *     *    *     *    *     *    *     *    *     *    *     *    *
GACTCTTAGC AACTTAAGTT TCAAACCGTG ACGAACCAAT AAAATTTGAC AAATTAATCA CTTTAAGTGC CTAGTGGATC
      .  570     .  580     .  590     .  600     .  610     .  620     .  630     .  640
      *    *     *    *     *    *     *    *     *    *     *    *     *    *     *    *
AGCGTCTAGG TTGGGAACCC CTCTACCTGC GTTTGATTCA CCAAGCTATC AAAATGGTCA GACACTGTGC TGCAATGCAC
      .  650     .  660     .  670     .  680     .  690     .  700     .  710     .  720
      *    *     *    *     *    *     *    *     *    *     *    *     *    *     *    *
AATTGGAGCA TTTCACATGC GTTGCATGAA TTATTCCTTG GGTTAGGAAA CCTTTGAAAT ACCTTGACTA AGGTAAAAAA
      .  730     .  740     .  750     .  760     .  770     .  780     .  790     .  800
      *    *     *    *     *    *     *    *     *    *     *    *     *    *     *    *
AAAAACTTGA CAAATTAATA AATATTAATA TTGATTTTGT ACGTACACGA CTTAACCAAA CTCTCAATGA TTTATTGATT
      .  810     .  820     .  830     .  840     .  850     .  860     .  870     .  880
      *    *     *    *     *    *     *    *     *    *     *    *     *    *     *    *
TCTAATATAT ATATTAATAA NGTANGTCTA ATTGGATCAT TCATGATCTA CAGCCATCAC ATCTCAGATG ATTTTCTTGC
      .  890     .  900     .  910     .  920     .  930     .  940     .  950     .  960
      *    *     *    *     *    *     *    *     *    *     *    *     *    *     *    *
AATGAATTGC CTAAGCTGGC GTTATTATCT TTTTTTCATA ATACAGTTTT AAAAAAGGGT ACGTATTGGA GCTGGTGATG
      .  970     .  980     .  990     . 1000     . 1010     . 1020     . 1030     . 1040
      *    *     *    *     *    *     *    *     *    *     *    *     *    *     *    *
ACTTCTTAAG AAACAACAAA TTAACGCCAT AGCTATTTGA TTTATATATC CAAAAGGAGA AAATGTATAA GATCGTTGCT
                                                                 >CAAT_box
      . 1050     . 1060     . 1070     . 1080     . 1090     .  | 1100    . 1110     . 1120
      *    *     *    *     *    *     *    *     *    *     *  |  *      *    *     *    *
TACTTAATTT GCAGGCTAGG TTAATTGACA TCAAATAATT GAAGAGTACG TAGGGCCAAT GTTGCTGAGA TCTAGCATCA
      . 1130     . 1140     . 1150     . 1160     . 1170     . 1180     . 1190     . 1200
      *    *     *    *     *    *     *    *     *    *     *    *     *    *     *    *
ATAATAGGAT TTGGCTTGTC GATCGATCAT CTTTATTTAA TTGAGAGGTA TGTATCCATA TGTTTTCTGA AATTAAAATA
                                                                 >TATA_box
      . 1210     . 1220     . 1230     . 1240     . 1250     . 1260     . 1270     . 1280
      *    *     *    *     *    *     *    *     *    *     *  |  *     *    *     *    *
TTACCTAATA ATTGAGCTGA AACTGTAGTG AATTTAACCT TTTCTAAGTT CTGCCCATAT ATAACATACC ACATAGGTAG
             >TATA_box
>Start_codon
      . 1290     . |1300      . 1310     . 1320     . 1330     . 1340     . 1350     .      |
      *    *     * |  *       *    *     *    *     *    *     *    *     *    *     *      |
CTGATCGATC GATCATATAT ATGTACTTAG GGTTCTGATC AGTATCAATA TCGATCACAA GTGCTGATAA TTAAAC ATG
Met>
```

Fig. 3A

```
___>
       1360          1370          1380          1390          1400          1410          1420
         *             *             *             *             *             *             *
GTT CTT CAA GGT AAG GTG GAG GCT GAC ATT GAA ATC TCA GCA CCT GCT GAC AAG TTC TAC AAC CTC
Val Leu Gln Gly Lys Val Glu Ala Asp Ile Glu Ile Ser Ala Pro Ala Asp Lys Phe Tyr Asn
Leu>
    ___a___a___a___a___a___a___a___a___a___DRU1
EXONI___a___a___a___a___a___a___a___a___a___>
       1430          1440          1450          1460          1470          1480          1490
         *             *             *             *             *             *             *
TTC AAG AGT GAG GCT CAC CAC GTC CCC AAA ACT TCT CAA ACT GGC ACC ATA ACC GGA GTT GCG GTG
Phe Lys Ser Glu Ala His His Val Pro Lys Thr Ser Gln Thr Gly Thr Ile Thr Gly Val Ala
Val>
    ___a___a___a___a___a___a___a___a___a___DRU1
EXONI___a___a___a___a___a___a___a___a___>
       1500          1510          1520          1530          1540          1550
         *             *             *             *             *             *
CAT GAA GGA GAC TGG GAA ACT GAT GGC TCC ATT AAG ATT TGG AAT TAT GCA ATA G GTAA
His Glu Gly Asp Trp Glu Thr Asp Gly Ser Ile Lys Ile Trp Asn Tyr Ala Ile Glu>
    ___a___a___a___a___a___a___a___DRU1 EXONI___a___a___a___a___a___a___a___a___>
                                                                              ___>
          1560          1570          1580          1590          1600          1610          1620          1630
            *             *             *             *             *             *             *             *
GCCATTATGT TGTTAGATTG TTAATTTAGA TTATTAACCA AAGCTGGCTT TGAATCACTA CAATATATAT TAGGGCACGC
_____c_____c_____c_____INTRON
I_____c_____c_____c_____>
          1640          1650          1660          1670          1680          1690          1700
            *             *             *             *             *             *             *
CAGTACAGAT TTTCTGTTTA TAATTGTTTC AGTGATTATT TTCTTACAAA TATAG AG GGC GAA GTG GGA ACA TTC
                                                             Gly Glu Val Gly Thr
Phe>
                                                           __b___DRU1 EXON
II____b___>
          _____c_____c___INTRON I_____c_____c_____>
       1710          1720          1730          1740          1750          1760          1770
         *             *             *             *             *             *             *
AAG GAG AAA GTA GAG CTA GAC GAT GTG AAC AAG GCA ATA ATT CTG AAT GGG TTG GAA GGA GAT GTG
Lys Glu Lys Val Glu Leu Asp Asp Val Asn Lys Ala Ile Ile Leu Asn Gly Leu Glu Gly Asp
Val>
    ___b___b___b___b___b___b___b___b___b_DRU1 EXON
II__b___b___b___b___b___b___b___b___b___>
       1780          1790          1800          1810          1820          1830
         *             *             *             *             *             *
TTC CAG TAT TAC AAG AGC TTC AAG CCC GTC TAT CAA TTC ACT CAA AAG AAT GAT GGC AGC AGC ATT
Phe Gln Tyr Tyr Lys Ser Phe Lys Pro Val Tyr Gln Phe Thr Gln Lys Asn Asp Gly Ser Ser
Ile>
    ___b___b___b___b___b___b___b___b___b_DRU1 EXON
II__b___b___b___b___b___b___b___b___b___>
       1840          1850          1860          1870          1880          1890          1900
         *             *             *             *             *             *             *
GCC AAA GTG TCC ATT GAA TAT GAG AAA CTG AGT GAG GAA GTT GCA GAT CCA AAT AAG TAC ATT CGC
Ala Lys Val Ser Ile Glu Tyr Glu Lys Leu Ser Glu Glu Val Ala Asp Pro Asn Lys Tyr Ile
Arg>
    ___b___b___b___b___b___b___b___b___b_DRU1 EXON
II__b___b___b___b___b___b___b___b___b___>
        1910          1920          1930          1940          1950          1960          1970
          *             *             *             *             *             *             *
TTG ATG ACT AAT ATC GTC AAG GAT CTT GAT GCC CAC TTC ATC AAG GCA TAA AAGGGA TATTATAATA
Leu Met Thr Asn Ile Val Lys Asp Leu Asp Ala His Phe Ile Lys Ala ***>
    ___b___b___b___b___b___b___DRU1 EXON II___b___b___b___b___b___b___>
          1980          1990          2000          2010          2020          2030          2040          2050
            *             *             *             *             *             *             *             *
AATCAAGCAT ATGAAACACG ATGAAAAGAG AGCTAGCCAC TATCTACTGC TGGTTTATAA GTTTAAAGAT AATCATGTGA
        >Nsi_I
            |
          2060          2070          2080          2090          2100          2110          2120          2130
            *|            *             *             *             *             *             *             *
ACGTTGTAAT GCATGCTTTG TTTGGTTACT TCGTTTTAAT GTCTTGTTAT GCACTAATAC CGTCAGTGTA ATAAAAGCTA

>poly(A)_site
          2140          2150          2160          2170          2180          2190          2200          2210
            *             *             *             *             *             *             *             *|
GTGTGAAAGG ATCTGATATA TTGTGATGTA TCATGTATTC AACTACCAAC TATATATGGT ATCATATTTA TATATCAAAT
AAA
```

Fig. 3B

Leaf  I  II  III  IV
      Receptacle 1  2  3  4  5

Leaf  Green receptacle  Ripe receptacle  Green drupelet  Ripe drupelet
Raspberry 1  2  3  4  5

Green  Mature green  Breaker  Orange  Ripe

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 30 amino acids
      (B) TYPE: amino acid
      (D) TOPOLOGY: linear (ii) MOLECULE TYPE: protein (iii) HYPOTHETICAL: NO (vi) ORIGINAL SOURCE:
      (C) INDIVIDUAL ISOLATE: amino terminal drupel sequence (xi) SEQUENCE DESCRIPTION: SEQ ID NO:1:

```
Val Leu Gln Gly Lys Val Glu Ala Asp Ile Glu Ile Ser Ala Pro Ala
1               5                   10                  15

Ala Lys Phe Tyr Asn Leu Phe Lys Ser Glu Ala Xaa Trp Val
            20                  25                  30
```

(2) INFORMATION FOR SEQ ID NO:2:

(i) SEQUENCE CHARACTERISTICS:
      (A) LENGTH: 30 base pairs (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: dTRANDOM primer (xi) SEQUENCE DESCRIPTION: SEQ ID NO:2:

TAGGCTCGTA GACTCTTTTT TTTTTTTTTT                                        30

(2) INFORMATION FOR SEQ ID NO:3:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (iii) HYPOTHETICAL: NO (v) FRAGMENT TYPE: internal (vi) ORIGINAL SOURCE:
            (C) INDIVIDUAL ISOLATE: dru1 partial amino acid sequence (xi) SEQUENCE DESCRIPTION: SEQ ID NO:3:

Gln Gly Lys Val Glu Ala Asp
1               5

(2) INFORMATION FOR SEQ ID NO:4:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: reverse translated sequence of SEQ
                ID NO:3

(ix) FEATURE:
            (A) NAME/KEY: other
            (B) LOCATION: 3, 6, 9, 12, 15, 18
            (C) OTHER INFORMATION: /note:= "where R is either G or A;
                where N is either G, A, T or C"

(xi) SEQUENCE DESCRIPTION: SEQ ID NO:4:

CARGGNAARG TNGARCGNGA                                                   20

(2) INFORMATION FOR SEQ ID NO:5:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: DrupeRAN18 primer (xi) SEQUENCE DESCRIPTION: SEQ ID NO:5:

TAGGCTCGTA GACTCTTT                                                         18

(2) INFORMATION FOR SEQ ID NO:6:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: DruGen 5' primer (xi) SEQUENCE DESCRIPTION: SEQ ID NO:6:

AAGGTGGAGG CTGACATT                                                         18

(2) INFORMATION FOR SEQ ID NO:7:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: DruGen 3' primer (xi) SEQUENCE DESCRIPTION: SEQ ID NO:7:

CTGACGGTAT TAGTGCATAA CA                                                    22

(2) INFORMATION FOR SEQ ID NO:8:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: DruInvUp primer (xi) SEQUENCE DESCRIPTION: SEQ ID NO:8:

TGAATGGGTT GGAAGGAGAT GTGT                                                  24

(2) INFORMATION FOR SEQ ID NO:9:

(i) SEQUENCE CHARACTERISTICS:

(A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: DruInvLow primer (xi) SEQUENCE DESCRIPTION: SEQ ID NO:9:

ATGGTGCCAG TTTGAGAAGT TTTG                                          24

(2) INFORMATION FOR SEQ ID NO:10:

(i) SEQUENCE CHARACTERISTICS:
        (A) LENGTH: 751 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: pAG301 insert, dru1 cDNA clone (xi) SEQUENCE DESCRIPTION: SEQ ID NO:10:

CAGGGAAAGG TGGAGGCTGA CATTGAAATC TCAGCACCTG CTGACAAGTT CTACAACCTC     60

TTCAAGAGTG AGGCTCACCA CGTCCCCAAA ACTTCTCAAA CTGGCACCAT AACCGGAGTT    120

GCGGTGCATG AAGGAGACTG GGAAACTGAT GGCTCCATTA AGATTTGGAA TTATGCAATA    180

GAGGGCGAAG TGGGAACATT CAAGGAGAAA GTAGAGCTAG ACGATGTGAA CAAGGCAATA    240

ATTCTGAATG GGTTGGAAGG AGATGTGTTC CAGTATTACA AGAGCTTCAA GCCCGTCTAT    300

CAATTCACTC AAAAGAATGA TGGCAGCAGC ATTGCCAAAG TGTCCATTGA ATATGAGAAA    360

CTGAGTGAGG AAGTTGCAGA TCCAAATAAG TACATTCGCT TGATGACTAA TATCGTCAAG    420

GATCTTGATG CCCACTTCAT CAAGGCATAA AAGGGATATT ATAATAAATC AAGCATATGA    480

AACACGATGA AAAGAGAGCT AGCCACTATC TACTGCTGGT TTATAAGTTT AAAGATAATC    540

ATGTGAACGT TGTAATGCAT GCTTTGTTTG GTTACTTCGT TTTAATGTCT TGTTATGCAC    600

TAATACCGTC AGTGTAATAA AAGCTAGTGT GAAAGGATCT GATATATTGT GATGTATCAT    660

GTATTCAACT ACCAACTATA TATGGTATCA TATTTATATA TCAAATAAAT TAATGTGAAA    720

AAAAAAAAAA AAAAAAGAG TCTACGAGCC T                                   751

(2) INFORMATION FOR SEQ ID NO:11:

(i) SEQUENCE CHARACTERISTICS:
        (A) LENGTH: 745 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:

(C) INDIVIDUAL ISOLATE: pAG302, dru1 genomic clone (xi) SEQUENCE DESCRIPTION: SEQ ID NO:11:

| | | | | | |
|---|---|---|---|---|---|
| AAGGTGGAGG | CTGACATTGA | AATCTCAGCA | CCTGCTGACA | AGTTCTACAA | CCTCTTCAAG | 60 |
| AGTGAGGCTC | ACCACGTCCC | CAAAACTTCT | CAAACTGGCA | CCATAACCGG | AGTTGCGGTG | 120 |
| CATGAAGGAG | ACTGGGAAAC | TGATGGCTCC | ATTAAGATTT | GGAATTATGC | AATAGGTAAG | 180 |
| CCATTATGTT | GTTAGATTGT | TAATTTAGAT | TATTAACCAA | AGCTGGCTTT | GAATCACTAC | 240 |
| AATATATATT | AGGGCACGCC | AGTACAGATT | TTCTGTTTAT | AATTGTTTCA | GTGATTATTT | 300 |
| TCTTACAAAT | ATAGAGGGCG | AAGTGGGAAC | ATTCAAGGAG | AAAGTAGAGC | TAGACGATGT | 360 |
| GAACAAGGCA | ATAATTCTGA | ATGGGTTGGA | AGGAGATGTG | TTCCAGTATT | ACAAGAGCTT | 420 |
| CAAGCCCGTC | TATCAATTCA | CTCAAAAGAA | TGATGGCAGC | AGCATTGCCA | AAGTGTCCAT | 480 |
| TGAATATGAG | AAACTGAGTG | AGGAAGTTGC | AGATCCAAAT | AAGTACATTC | GCTTGATGAC | 540 |
| TAATATCGTC | AAGGATCTTG | ATGCCCACTT | CATCAAGGCA | TAAAAGGGAT | ATTATAATAA | 600 |
| ATCAAGCATA | TGAAACACGA | TGAAAAGAGA | GCTAGCCACT | ATCTACTGCT | GGTTTATAAG | 660 |
| TTTAAAGATA | ATCATGTGAA | CGTTGTAATG | CATGCTTTGT | TTGGTTACTT | CGTTTTAATG | 720 |
| TCTTGTTATG | CACTAATACC | GTCAG | | | | 745 |

(2) INFORMATION FOR SEQ ID NO:12:

(i) SEQUENCE CHARACTERISTICS:
        (A) LENGTH: 2213 base pairs
        (B) TYPE: nucleic acid
        (C) STRANDEDNESS: both
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: pAG310 insert sequence (xi) SEQUENCE DESCRIPTION: SEQ ID NO:12:

| | | | | | |
|---|---|---|---|---|---|
| ATGCATATCA | ACAACTACGA | ATAAAGAGAT | CAGCCTTTCC | GTATCTGGTG | GATGTTTGAG | 60 |
| TCGGTGATGA | CCATCTAATT | AAAGAAAGAA | GAAAAATTAT | ACATATTGTG | GACCTCCCCA | 120 |
| TATATAATTC | TTATCATCTT | TGTTACTGCC | ATTATGATTA | TAAATGATA | TTAAAGGGAT | 180 |
| GGTGTACCGT | GTACTAATCA | AATATCTACC | TGATCTTATT | GATTTGAAAG | ATCATAAAAA | 240 |
| GAAATTAAAA | TTGTTCAAAA | TAAACCCCTA | GAATTATATA | TAGTTCATTA | AGTTCAAATT | 300 |
| AATTCGTTTG | AAACGTGTTA | AGCAACCCTA | CAACGTACTA | AGCACCCTAG | CTCCCTTTGC | 360 |
| CTCTCGGCGG | TAAGAGGAGA | TATCCTCAGT | CGAATTATGA | GCCGATCGAG | GAAAGCTCGA | 420 |
| TCAGTTGGAA | AATCTTTCTT | TCTTATGGCC | AAGTTGTTTC | AAACAATATA | TTGAATTATT | 480 |
| GACTCTTAGC | AACTTAAGTT | TCAAACCGTG | ACGAACCAAT | AAAATTTGAC | AAATTAATCA | 540 |
| CTTTAAGTGC | CTAGTGGATC | AGCGTCTAGG | TTGGGAACCC | CTCTACCTGC | GTTTGATTCA | 600 |
| CCAAGCTATC | AAAATGGTCA | GACACTGTGC | TGCAATGCAC | AATTGGAGCA | TTTCACATGC | 660 |
| GTTGCATGAA | TTATTCCTTG | GGTTAGGAAA | CCTTTGAAAT | ACCTTGACTA | AGGTAAAAAA | 720 |
| AAAAACTTGA | CAAATTAATA | AATATTAATA | TTGATTTTGT | ACGTACACGA | CTTAACCAAA | 780 |
| CTCTCAATGA | TTTATTGATT | TCTAATATAT | ATATTAATAA | CGTACGTCTA | ATTGGATCAT | 840 |
| TCATGATCTA | CAGCCATCAC | ATCTCAGATG | ATTTTCTTGC | AATGAATTGC | CTAAGCTGGC | 900 |

```
GTTATTATCT TTTTTTCATA ATACAGTTTT AAAAAAGGGT ACGTATTGGA GCTGGTGATG      960

ACTTCTTAAG AAACAACAAA TTAACGCCAT AGCTATTTGA TTTATATATC CAAAAGGAGA     1020

AAATGTATAA GATCGTTGCT TACTTAATTT GCAGGCTAGG TTAATTGACA TCAAATAATT     1080

GAAGAGTACG TAGGGCCAAT GTTGCTGAGA TCTAGCATCA ATAATAGGAT TTGGCTTGTC     1140

GATCGATCAT CTTTATTTAA TTGAGAGGTA TGTATCCATA TGTTTTCTGA AATTAAAATA     1200

TTACCTAATA ATTGAGCTGA AACTGTAGTG AATTTAACCT TTTCTAAGTT CTGCCCATAT     1260

ATAACATACC ACATAGGTAG CTGATCGATC GATCATATAT ATGTACTTAG GGTTCTGATC     1320

AGTATCAATA TCGATCACAA GTGCTGATAA TTAAACATGG TTCTTCAAGG TAAGGTGGAG     1380

GCTGACATTG AAATCTCAGC ACCTGCTGAC AAGTTCTACA ACCTCTTCAA GAGTGAGGCT     1440

CACCACGTCC CCAAAACTTC TCAAACTGGC ACCATAACCG GAGTTGCGGT GCATGAAGGA     1500

GACTGGGAAA CTGATGGCTC CATTAAGATT TGGAATTATG CAATAGGTAA GCCATTATGT     1560

TGTTAGATTG TTAATTTAGA TTATTAACCA AAGCTGGCTT TGAATCACTA CAATATATAT     1620

TAGGGCACGC CAGTACAGAT TTTCTGTTTA TAATTGTTTC AGTGATTATT TTCTTACAAA     1680

TATAGAGGGC GAAGTGGGAA CATTCAAGGA GAAAGTAGAG CTAGACGATG TGAACAAGGC     1740

AATAATTCTG AATGGGTTGG AAGGAGATGT GTTCCAGTAT TACAAGAGCT TCAAGCCCGT     1800

CTATCAATTC ACTCAAAAGA ATGATGGCAG CAGCATTGCC AAAGTGTCCA TTGAATATGA     1860

GAAACTGAGT GAGGAAGTTG CAGATCCAAA TAAGTACATT CGCTTGATGA CTAATATCGT     1920

CAAGGATCTT GATGCCCACT TCATCAAGGC ATAAAAGGGA TATTATAATA AATCAAGCAT     1980

ATGAAACACG ATGAAAAGAG AGCTAGCCAC TATCTACTGC TGGTTTATAA GTTTAAAGAT     2040

AATCATGTGA ACGTTGTAAT GCATGCTTTG TTTGGTTACT TCGTTTTAAT GTCTTGTTAT     2100

GCACTAATAC CGTCAGTGTA ATAAAAGCTA GTGTGAAAGG ATCTGATATA TTGTGATGTA     2160

TCATGTATTC AACTACCAAC TATATATGGT ATCATATTTA TATATCAAAT AAA            2213

(2) INFORMATION FOR SEQ ID NO:13:

(i) SEQUENCE CHARACTERISTICS:
        (A) LENGTH: 152 amino acids
        (B) TYPE: amino acid
        (D) TOPOLOGY: linear (ii) MOLECULE TYPE: protein (iii) HYPOTHETICAL: NO (iv) ANTI-SENSE: NO (vi) ORIGINAL SOURCE:
         (C) INDIVIDUAL ISOLATE: predicted amino acid coding sequence
             of dru1

(xi) SEQUENCE DESCRIPTION: SEQ ID NO:13:

Met Val Leu Gln Gly Lys Val Glu Ala Asp Ile Glu Ile Ser Ala Pro
1               5                   10                  15

Ala Asp Lys Phe Tyr Asn Leu Phe Lys Ser Glu Ala His His Val Pro
            20                  25                  30

Lys Thr Ser Gln Thr Gly Thr Ile Thr Gly Val Ala Val His Glu Gly
        35                  40                  45

Asp Trp Glu Thr Asp Gly Ser Ile Lys Ile Trp Asn Tyr Ala Ile Glu
    50                  55                  60

Gly Glu Val Gly Thr Phe Lys Glu Lys Val Glu Leu Asp Asp Val Asn
65                  70                  75                  80

Lys Ala Ile Ile Leu Asn Gly Leu Glu Gly Asp Val Phe Gln Tyr Tyr
```

```
                85                    90                   95
Lys Ser Phe Lys Pro Val Tyr Gln Phe Thr Gln Lys Asn Asp Gly Ser
                100                   105                  110

Ser Ile Ala Lys Val Ser Ile Glu Tyr Glu Lys Leu Ser Glu Glu Val
        115                 120                 125

Ala Asp Pro Asn Lys Tyr Ile Arg Leu Met Thr Asn Ile Val Lys Asp
        130                 135                 140

Leu Asp Ala His Phe Ile Lys Ala
145                 150
```

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: DruPro5'RI primer (xi) SEQUENCE DESCRIPTION: SEQ ID NO:14:

```
GAGAATTCCC CGGGCAGATC AACAACTAC                              29
```

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: DruPro3' primer (xi) SEQUENCE DESCRIPTION: SEQ ID NO:15:

```
GCGCGGCCAT GGTTAATTAT CAG                                    23
```

(2) INFORMATION FOR SEQ ID NO:16:

(i) SEQUENCE CHARACTERISTICS:
        (A) LENGTH: 2145 base pairs
        (B) TYPE: nucleic acid
        (C) STRANDEDNESS: both
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: dru1 promoter:SAMase chimeric gene (xi) SEQUENCE DESCRIPTION: SEQ ID NO:16:

```
CCCGGGCAGA TCAACAACTA CGAATAAAGA GATCAGCCTT TCCGTATCTG GTGGATGTTT     60
```

```
GAGTCGGTGA TGACCATCTA ATTAAAGAAA GAAGAAAAAT TATACATATT GTGGACCTCC    120

CCATATATAA TTCTTATCAT CTTTGTTACT GCCATTATGA TTATAAAATG ATATTAAAGG    180

GATGGTGTAC CGTGTACTAA TCAAATATCT ACCTGATCTT ATTGATTTGA AAGATCATAA    240

AAAGAAATTA AAATTGTTCA AAATAAACCC CTAGAATTAT ATATAGTTCA TTAAGTTCAA    300

ATTAATTCGT TGAAACGTG TTAAGCAACC CTACAACGTA CTAAGCACCC TAGCTCCCTT    360

TGCCTCTCGG CGGTAAGAGG AGATATCCTC AGTCGAATTA TGAGCCGATC GAGGAAAGCT    420

CGATCAGTTG GAAAATCTTT CTTTCTTATG CCAAGTTGT TTCAAACAAT ATATTGAATT    480

ATTGACTCTT AGCAACTTAA GTTTCAAACC GTGACGAACC AATAAAATTT GACAAATTAA    540

TCACTTTAAG TGCCTAGTGG ATCAGCGTCT AGGTTGGGAA CCCCTCTACC TGCGTTTGAT    600

TCACCAAGCT ATCAAAATGG TCAGACACTG TGCTGCAATG CACAATTGGA GCATTTCACA    660

TGCGTTGCAT GAATTATTCC TTGGGTTAGG AAACCTTTGA ATACCTTGA CTAAGGTAAA    720

AAAAAAAACT TGACAAATTA ATAAATATTA ATATTGATTT TGTACGTACA CGACTTAACC    780

AAACTCTCAA TGATTTATTG ATTTCTAATA TATATATTAA TAACGTACGT CTAATTGGAT    840

CATTCATGAT CTACAGCCAT CACATCTCAG ATGATTTTCT TGCAATGAAT TGCCTAAGCT    900

GGCGTTATTA TCTTTTTTC ATAATACAGT TTTAAAAAAG GGTACGTATT GGAGCTGGTG    960

ATGACTTCTT AAGAAACAAC AAATTAACGC CATAGCTATT TGATTTATAT ATCCAAAAGG   1020

AGAAAATGTA TAAGATCGTT GCTTACTTAA TTTGCAGGCT AGGTTAATTG ACATCAAATA   1080

ATTGAAGAGT ACGTAGGGCC AATGTTGCTG AGATCTAGCA TCAATAATAG GATTTGGCTT   1140

GTCGATCGAT CATCTTTATT TAATTGAGAG GTATGTATCC ATATGTTTTC TGAAATTAAA   1200

ATATTACCTA ATAATTGAGC TGAAACTGTA GTGAATTTAA CCTTTTCTAA GTTCTGCCCA   1260

TATATAACAT ACCACATAGG TAGCTGATCG ATCGATCATA TATATGTACT TAGGGTTCTG   1320

ATCAGTATCA ATATCGATCA CAAGTGCTGA TAATTAACCA TGGTTTTCAC TAAAGAGCCT   1380

GCGAACGTCT TCTATGTACT GGTTTCCGCT TTCCGTTCTA ACCTCTGCGA TGAGGTGAAT   1440

ATGAGCAGAC ACCGCCACAT GGTAAGCACT TTACGTGCCG CACCGGGTCT TTATGGCTCC   1500

GTTGAGTCAA CCGATTTGAC CGGGTGCTAT CGTGAGGCAA TCTCAAGCGC ACCAACTGAG   1560

GAAAAAACTG TTCGTGTACG CTACAAGGAC AAAGCGCAGC CACTCAATGT TGCACGCCTA   1620

GCTTCTAATG AGTGGGAGCA AGATTGCGTA CTGGTATACA AATCACAGAC TCACACGGCT   1680

GGTCTGGTGT ACGCTAAAGG TATCGACGGG TATAAGGCTG AACGTCTGCC GGGTAGTTTC   1740

CAAGAGGTTC CTAAAGGCGC ACCGCTGCAA GGCTGCTTCA CTATTGATGA GTTCGGTCGC   1800

CGCTGGCAAG TACAATAAGT GTTAAACTCA AGGTCATGCA CGATGCGTGG CGGATCGGGT   1860

ACCGAGCTCG AATTTCGACC TGCAGATCGT TCAAACATTT GGCAATAAAG TTTCTTAAGA   1920

TTGAATCCTG TTGCCGGTCT TGCGATGATT ATCATATAAT TTCTGTTGAA TTACGTTAAG   1980

CATGTAATAA TTAACATGTA ATGCATGACG TTATTTATGA GATGGGTTTT TATGATTAGA   2040

GTCCCGCAAT TATACATTTA ATACGCGATA GAAAACAAAA TATAGCGCGC AAACTAGGAT   2100

AAATTATCGC GCGCGGTGTC ATCTATGTTA CTAGATCTTC TAGAA              2145
```

(2) INFORMATION FOR SEQ ID NO:17:

(i) SEQUENCE CHARACTERISTICS:
        (A) LENGTH: 152 amino acids
        (B) TYPE: amino acid
        (D) TOPOLOGY: linear (ii) MOLECULE TYPE: protein (iii) HYPOTHETICAL: NO (vi) ORIGINAL SOURCE:
             (C) INDIVIDUAL ISOLATE: predicted amino acid coding sequence
                 of SEQ ID NO:16

(xi) SEQUENCE DESCRIPTION: SEQ ID NO:17:

Met Val Phe Thr Lys Glu Pro Ala Asn Val Phe Tyr Val Leu Val Ser
1               5                   10                  15

Ala Phe Arg Ser Asn Leu Cys Asp Glu Val Asn Met Ser Arg His Arg
            20                  25                  30

His Met Val Ser Thr Leu Arg Ala Ala Pro Gly Leu Tyr Gly Ser Val
        35                  40                  45

Glu Ser Thr Asp Leu Thr Gly Cys Tyr Arg Glu Ala Ile Ser Ser Ala
    50                  55                  60

Pro Thr Glu Glu Lys Thr Val Arg Val Arg Tyr Lys Asp Lys Ala Gln
65                  70                  75                  80

Pro Leu Asn Val Ala Arg Leu Ala Ser Asn Glu Trp Glu Gln Asp Cys
                85                  90                  95

Val Leu Val Tyr Lys Ser Gln Thr His Thr Ala Gly Leu Val Tyr Ala
            100                 105                 110

Lys Gly Ile Asp Gly Tyr Lys Ala Glu Arg Leu Pro Gly Ser Phe Gln
            115                 120                 125

Glu Val Pro Lys Gly Ala Pro Leu Gln Gly Cys Phe Thr Ile Asp Glu
            130                 135                 140

Phe Gly Arg Arg Trp Gln Val Gln
145                 150

(2) INFORMATION FOR SEQ ID NO:18:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: PGIP Nco5' Primer (xi) SEQUENCE DESCRIPTION: SEQ ID NO:18:

GGGGCTCCAT GGCTCATT                                                         18

(2) INFORMATION FOR SEQ ID NO:19:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: PGIP Pst3' Primer (xi) SEQUENCE DESCRIPTION: SEQ ID NO:19:

-continued

```
GGGCGAAAAA CCGTCTATCA G                                              21
```

(2) INFORMATION FOR SEQ ID NO:20:

(i) SEQUENCE CHARACTERISTICS:
        (A) LENGTH: 2917 base pairs
        (B) TYPE: nucleic acid
        (C) STRANDEDNESS: both
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: sequence of the dru1:PGIP chimeric
           gene (xi) SEQUENCE DESCRIPTION: SEQ ID NO:20:

```
GAATTCCCCG GGCAGATCAA CAACTACGAA TAAAGAGATC AGCCTTTCCG TATCTGGTGG      60
ATGTTTGAGT CGGTGATGAC CATCTAATTA AGAAAGAAG  AAAAATTATA CATATTGTGG     120
ACCTCCCCAT ATATAATTCT TATCATCTTT GTTACTGCCA TTATGATTAT AAAATGATAT     180
TAAAGGGATG GTGTACCGTG TACTAATCAA ATATCTACCT GATCTTATTG ATTTGAAAGA     240
TCATAAAAAG AAATTAAAAT TGTTCAAAAT AAACCCCTAG AATTATATAT AGTTCATTAA     300
GTTCAAATTA ATTCGTTTGA AACGTGTTAA GCAACCCTAC AACGTACTAA GCACCCTAGC     360
TCCCTTTGCC TCTCGGCGGT AAGAGGAGAT ATCCTCAGTC GAATTATGAG CCGATCGAGG     420
AAAGCTCGAT CAGTTGGAAA ATCTTTCTTT CTTATGGCCA AGTTGTTTCA AACAATATAT     480
TGAATTATTG ACTCTTAGCA ACTTAAGTTT CAAACCGTGA CGAACCAATA AAATTTGACA     540
AATTAATCAC TTTAAGTGCC TAGTGGATCA GCGTCTAGGT TGGGAACCCC TCTACCTGCG     600
TTTGATTCAC CAAGCTATCA AAATGGTCAG ACACTGTGCT GCAATGCACA ATTGGAGCAT     660
TTCACATGCG TTGCATGAAT TATTCCTTGG GTTAGGAAAC CTTTGAAATA CCTTGACTAA     720
GGTAAAAAAA AAAACTTGAC AAATTAATAA ATATTAATAT TGATTTTGTA CGTACACGAC     780
TTAACCAAAC TCTCAATGAT TTATTGATTT CTAATATATA TATTAATAAC GTACGTCTAA     840
TTGGATCATT CATGATCTAC AGCCATCACA TCTCAGATGA TTTTCTTGCA ATGAATTGCC     900
TAAGCTGGCG TTATTATCTT TTTTTCATAA TACAGTTTTA AAAAGGGTA  CGTATTGGAG     960
CTGGTGATGA CTTCTTAAGA AACAACAAAT TAACGCCATA GCTATTTGAT TTATATATCC    1020
AAAAGGAGAA AATGTATAAG ATCGTTGCTT ACTTAATTTG CAGGCTAGGT TAATTGACAT    1080
CAAATAATTG AAGAGTACGT AGGGCCAATG TTGCTGAGAT CTAGCATCAA TAATAGGATT    1140
TGGCTTGTCG ATCGATCATC TTTATTTAAT TGAGAGGTAT GTATCCATAT GTTTTCTGAA    1200
ATTAAAATAT TACCTAATAA TTGAGCTGAA ACTGTAGTGA ATTTAACCTT TTCTAAGTTC    1260
TGCCCATATA TAACATACCA CATAGGTAGC TGATCGATCG ATCATATATA TGTACTTAGG    1320
GTTCTGATCA GTATCAATAT CGATCACAAG TGCTGATAAT TAACCATGGC TCAATTCAAT    1380
ATCCCAGTAA CCATGTCTTC AAGCTTAAGC ATAATTTTGG TCATTCTTGT ATCTTTGAGA    1440
ACTGCACTCT CAGAGCTATG CAACCCACAA GATAAGCAAG CCCTTCTCCA AATCAAGAAA    1500
GACCTTGGCA ACCCAACCAC TCTCTCTTCA TGGCTTCCAA CCACCGACTG TTGTAACAGA    1560
ACCTGGCTAG GTGTTTTATG CGACACCGAC ACCCAAACAT ATCGCGTCAA CAACCTCGAC    1620
CTCTCCGGCC ATAACCTCCC AAAACCCTAC CCTATCCCTT CCTCCCTCGC CAACCTCCCC    1680
TACCTCAATT TTCTATACAT TGGCGGCATC AATAACCTCG TCGGTCCAAT CCCCCCCGCC    1740
```

-continued

```
ATCGCTAAAC TCACCCAACT CCACTATCTC TATATCACTC ACACCAATGT CTCCGGCGCA    1800

ATACCCGATT TCTTGTCACA GATCAAAACC CTCGTCACCC TCGACTTCTC CTACAACGCC    1860

CTCTCCGGCA CCCTCCCTCC CTCCATCTCT TCTCTCCCCA ACCTCGGAGG AATCACATTC    1920

GACGGCAACC GAATCTCCGG CGCCATCCCC GACTCCTACG GCTCGTTTTC GAAGCTGTTT    1980

ACGGCGATGA CCATCTCCCG CAACCGCCTC ACCGGGAAGA TTCCACCGAC GTTTGCGAAT    2040

CTGAACCTGG CGTTCGTTGA CTTGTCTCGG AACATGCTGG AGGGTGACGC GTCGGTGTTG    2100

TTCGGGTCAG ATAAGAACAC GAAGAAGATA CATCTGGCGA AGAACTCTCT TGCTTTTGAT    2160

TTGGGGAAAG TGGGGTTGTC AAAGAACTTG AACGGGTTGG ATCTGAGGAA CAACCGTATC    2220

TATGGGACGC TACCTCAGGG ACTAACGCAG CTAAAGTTTC TGCAAAGTTT AAATGTGAGC    2280

TTCAACAATC TGTGCGGTGA GATTCCTCAA GGTGGGAACT TGAAAAGGTT TGACGTTTCT    2340

TCTTATGCCA ACAACAAGTG CTTGTGTGGT TCTCCTCTTC CTTCCTGCAC TTAACCATTT    2400

CCAGATTCGG TAATTATGGA TGCATCATGT TTGCCTTTCT ATGAACATCA ATAATGATAC    2460

AAGTGTAAAA ATAAAAATAA ATTTATGATA TATAATAAAC GTCTTGTATC ATTATTTTTA    2520

TCCTAAAGTG AATTATAATA TTTGCTGATA AAAAAAAGCT CTCTCTCATA GGTAAGTATA    2580

TTTTTTAATA CATTTGACTG AAATAACATA TTCTCTGTAT GTACGTCGTA CTTAGGATCC    2640

CCCGGGCTGC AGATCGTTCA AACATTTGGC AATAAAGTTT CTTAAGATTG AATCCTGTTG    2700

CCGGTCTTGC GATGATTATC ATATAATTTC TGTTGAATTA CGTTAAGCAT GTAATAATTA    2760

ACATGTAATG CATGACGTTA TTTATGAGAT GGGTTTTTAT GATTAGAGTC CCGCAATTAT    2820

ACATTTAATA CGCGATAGAA AACAAAATAT AGCGCGCAAA CTAGGATAAA TTATCGCGCG    2880

CGGTGTCATC TATGTTACTA GATCTTCTAG AAAGCTT                              2917
```

(2) INFORMATION FOR SEQ ID NO:21:

(i) SEQUENCE CHARACTERISTICS:
        (A) LENGTH: 342 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: predicted amino acid coding sequence
            of SEQ ID NO:20

(xi) SEQUENCE DESCRIPTION: SEQ ID NO:21:

```
Met Ala Gln Phe Asn Ile Pro Val Thr Met Ser Ser Ser Leu Ser Ile
1               5                  10                  15

Ile Leu Val Ile Leu Val Ser Leu Arg Thr Ala Leu Ser Glu Leu Cys
            20                  25                  30

Asn Pro Gln Asp Lys Gln Ala Leu Leu Gln Ile Lys Lys Asp Leu Gly
        35                  40                  45

Asn Pro Thr Thr Leu Ser Ser Trp Leu Pro Thr Asp Cys Cys Asn
    50                  55                  60

Arg Thr Trp Leu Gly Val Leu Cys Asp Thr Asp Thr Gln Thr Tyr Arg
65                  70                  75                  80

Val Asn Asn Leu Asp Leu Ser Gly His Asn Leu Pro Lys Pro Tyr Pro
                85                  90                  95

Ile Pro Ser Ser Leu Ala Asn Leu Pro Tyr Leu Asn Phe Leu Tyr Ile
            100                 105                 110
```

```
Gly Gly Ile Asn Asn Leu Val Gly Pro Ile Pro Pro Ala Ile Ala Lys
            115                 120                 125

Leu Thr Gln Leu His Tyr Leu Tyr Ile Thr His Thr Asn Val Ser Gly
        130                 135                 140

Ala Ile Pro Asp Phe Leu Ser Gln Ile Lys Thr Leu Val Thr Leu Asp
145                 150                 155                 160

Phe Ser Tyr Asn Ala Leu Ser Gly Thr Leu Pro Pro Ser Ile Ser Ser
                165                 170                 175

Leu Pro Asn Leu Gly Gly Ile Thr Phe Asp Gly Asn Arg Ile Ser Gly
            180                 185                 190

Ala Ile Pro Asp Ser Tyr Gly Ser Phe Ser Lys Leu Phe Thr Ala Met
            195                 200                 205

Thr Ile Ser Arg Asn Arg Leu Thr Gly Lys Ile Pro Pro Thr Phe Ala
        210                 215                 220

Asn Leu Asn Leu Ala Phe Val Asp Leu Ser Arg Asn Met Leu Glu Gly
225                 230                 235                 240

Asp Ala Ser Val Leu Phe Gly Ser Asp Lys Asn Thr Lys Lys Ile His
                245                 250                 255

Leu Ala Lys Asn Ser Leu Ala Phe Asp Leu Gly Lys Val Gly Leu Ser
            260                 265                 270

Lys Asn Leu Asn Gly Leu Asp Leu Arg Asn Asn Arg Ile Tyr Gly Thr
        275                 280                 285

Leu Pro Gln Gly Leu Thr Gln Leu Lys Phe Leu Gln Ser Leu Asn Val
290                 295                 300

Ser Phe Asn Asn Leu Cys Gly Glu Ile Pro Gln Gly Gly Asn Leu Lys
305                 310                 315                 320

Arg Phe Asp Val Ser Ser Tyr Ala Asn Asn Lys Cys Leu Cys Gly Ser
                325                 330                 335

Pro Leu Pro Ser Cys Thr
            340

(2) INFORMATION FOR SEQ ID NO:22:

(i) SEQUENCE CHARACTERISTICS:
        (A) LENGTH: 1356 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: Exemplary dru1 promoter sequence (xi) SEQUENCE DESCRIPTION: SEQ ID NO:22:

ATGCATATCA ACAACTACGA ATAAAGAGAT CAGCCTTTCC GTATCTGGTG GATGTTTGAG      60

TCGGTGATGA CCATCTAATT AAAGAAAGAA GAAAAATTAT ACATATTGTG ACCTCCCCA     120

TATATAATTC TTATCATCTT TGTTACTGCC ATTATGATTA TAAAATGATA TTAAAGGGAT    180

GGTGTACCGT GTACTAATCA AATATCTACC TGATCTTATT GATTTGAAAG ATCATAAAAA    240

GAAATTAAAA TTGTTCAAAA TAAACCCCTA GAATTATATA TAGTTCATTA AGTTCAAATT    300

AATTCGTTTG AAACGTGTTA AGCAACCCTA CAACGTACTA AGCACCCTAG CTCCCTTTGC    360

CTCTCGGCGG TAAGAGGAGA TATCCTCAGT CGAATTATGA GCCGATCGAG GAAAGCTCGA    420

TCAGTTGGAA AATCTTTCTT TCTTATGGCC AAGTTGTTTC AAACAATATA TTGAATTATT    480
```

```
GACTCTTAGC AACTTAAGTT TCAAACCGTG ACGAACCAAT AAAATTTGAC AAATTAATCA      540

CTTTAAGTGC CTAGTGGATC AGCGTCTAGG TTGGGAACCC CTCTACCTGC GTTTGATTCA      600

CCAAGCTATC AAAATGGTCA GACACTGTGC TGCAATGCAC AATTGGAGCA TTTCACATGC      660

GTTGCATGAA TTATTCCTTG GGTTAGGAAA CCTTTGAAAT ACCTTGACTA AGGTAAAAAA      720

AAAAACTTGA CAAATTAATA AATATTAATA TTGATTTTGT ACGTACACGA CTTAACCAAA      780

CTCTCAATGA TTTATTGATT TCTAATATAT ATATTAATAA CGTACGTCTA ATTGGATCAT      840

TCATGATCTA CAGCCATCAC ATCTCAGATG ATTTTCTTGC AATGAATTGC CTAAGCTGGC      900

GTTATTATCT TTTTTTCATA ATACAGTTTT AAAAAAGGGT ACGTATTGGA GCTGGTGATG      960

ACTTCTTAAG AAACAACAAA TTAACGCCAT AGCTATTTGA TTTATATATC CAAAAGGAGA     1020

AAATGTATAA GATCGTTGCT TACTTAATTT GCAGGCTAGG TTAATTGACA TCAAATAATT     1080

GAAGAGTACG TAGGGCCAAT GTTGCTGAGA TCTAGCATCA ATAATAGGAT TTGGCTTGTC     1140

GATCGATCAT CTTTATTTAA TTGAGAGGTA TGTATCCATA TGTTTTCTGA AATTAAAATA     1200

TTACCTAATA ATTGAGCTGA AACTGTAGTG AATTTAACCT TTTCTAAGTT CTGCCCATAT     1260

ATAACATACC ACATAGGTAG CTGATCGATC GATCATATAT ATGTACTTAG GGTTCTGATC     1320

AGTATCAATA TCGATCACAA GTGCTGATAA TTAAAC                                1356
```

(2) INFORMATION FOR SEQ ID NO:23:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO (vi) ORIGINAL SOURCE:
        (C) INDIVIDUAL ISOLATE: drupelet mRNA poly A region (Fig 2A)

(xi) SEQUENCE DESCRIPTION: SEQ ID NO:23:

```
AAAAAAAAAA                                                              10
```

(2) INFORMATION FOR SEQ ID NO:24:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: first cDNA strand (Fig 2A)

(ix) FEATURE:
        (A) NAME/KEY: Other
        (B) LOCATION: 3, 6, 9, 12, 15, 18, 21, 23, 24
        (D) OTHER INFORMATION: /note= "where N is either
            G, A, T or C; where Y is either C or T; where R
            is either G or A"

(xi) SEQUENCE DESCRIPTION: SEQ ID NO:24:

TCNGCYTCNA CYTTNCCYTG NARNAC                    26

(2) INFORMATION FOR SEQ ID NO:25:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: first round PCR (Fig 2A)

(xi) SEQUENCE DESCRIPTION: SEQ ID NO:25:

AAAAAAAAAA GAGTCTACGA GCCTA                    25

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: second round amplification cDNA (Fig 2A)

(ix) FEATURE:
        (A) NAME/KEY: Other
        (B) LOCATION: 3, 6, 9, 12, 15, 18
        (D) OTHER INFORMATION: /note= "where N is either G,
            A, T or C; where Y is either C or T; where R is
            either G or A"

(xi) SEQUENCE DESCRIPTION: SEQ ID NO:26:

TCNGCYTCNA CYTTNCCYTG                    20

(2) INFORMATION FOR SEQ ID NO:27:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: amplified dru1 cDNA (Fig 2A)

(xi) SEQUENCE DESCRIPTION: SEQ ID NO:27:

AAAAAAAAAA AAAAAAAAAA GAGTCTACGA GCCTA                    35

PLANT TISSUE/STAGE SPECIFIC PROMOTERS FOR REGULATED EXPRESSION OF TRANSGENES IN PLANTS This application is a divisional of application Ser. No. 08/592,936, filed Jan. 29, 1996, now U.S. Pat. No. 5,783,393 which is hereby incorporated by reference.

FIELD OF THE INVENTION

The present invention relates to the identification and characterization of tissue and/or stage specific plant promoters and compositions and methods employing such promoters.

REFERENCES

Ausubel, F. M., et al., in CURRENT PROTOCOLS IN MOLECULAR BIOLOGY, John Wiley and Sons, Inc., Media PA (1992).

Becker, D., et al., *Plant Mol. Biol.* 20:1195–1197 (1992).

Bellini, C., et al., *Bio/Technol* 7(5):503–508 (1989).

Benfey, P. N., et al., *Science* 250:959–966 (1990).

Bestwick, R. K., et al., PCT International Publication No. WO 95/35387, published Dec. 28, 1995.

Bevan, M. W., et al., *Nuc. Acid Res.* 11:369–385 (1983).

Chalfie, M., et al., *Science* 263:802–805 (1994).

Chang, S., et al., *Plant Mol. Biol. Reporter* 11(2):113–116 (1993).

Comai, L. and Coning, A. J., U.S. Pat. No. 5,187,267, issued Feb. 16, 1993.

Cordes, S., et al., *The Plant Cell* 1:1025–1034 (1989).

Dayhoff, M. O., in ATLAS OF PROTEIN SEQUENCE AND STRUCTURE Vol. 5, National Biomedical Research Foundation, pp. 101–110, and Supplement 2 to this volume, pp. 1–10 (1972).

Depicker, A., et al., *J. Mol. Appl. Genet.* 1:561–573 (1982).

Dhaese, P., et al., *EMBO Journal* 2:419–426 (1983).

Doyle, J. J. and Doyle, J. L., *Focus* 12:13–15 (1990).

Ferro, A. J., et al., U.S. Pat. No. 5,416,250, issued May 16, 1995.

Gelvin, S. B., and Schilperoot, R. A., *Plant Mol. Bio.* (1988).

Hajdukiewicz, P., et al., *Plant Mol. Bio.* 25:989–994 (1994).

Hamilton, A. J., et al., *Nature* 346:284–287 (1990).

Herreraestrella, L., et al., *World Journal of Microbiology & Biotechnology.* 11(4):383–392 (1995).

Holdsworth, M. J., et al., *Nuc. Acids Res.* 15:731–739 (1987).

Houck, C. M. and Pear, J. R., U.S. Pat. No. 4,943,674, issued Jul. 24, 1990.

Hughes, J. A., et al., *J. Bact.* 169:3625–3632 (1987).

Jefferson, R. A., et al., *EMBO J.* 6:3901 (1987a).

Jefferson, R. A., *Plant Mol. Biol. Rep.* 5:387 (1987b).

Jorgensen, R. A., et al., U.S. Pat. No. 5,034,323, issued Jul. 23, 1991.

Jorgensen, R. A., et al., U.S. Pat. No. 5,231,020, issued Jul. 27, 1993.

Kawasaki, E. S., et al., in PCR TECHNOLOGY: PRINCIPLES AND APPLICATIONS OF DNA AMPLIFICATION (H. A. Erlich, ed.) Stockton Press (1989).

Klee, H. J., et al., *Plant Cell* 3:1187–1193 (1991).

Klein, T. M., et al., *PNAS (USA)* 85(22):8502–8505 (1988).

Kyte, J., and Doolittle, R. F., *J. Mol. Biol.* 157:105–132 (1982).

Laemelli, U. K., *Nature* 227:680–685 (1970).

Li, Q., and Hunt, A. G., *Plant Mol. Biol.* 28:927–934 (1995).

Lin, E., et al., *Plant Mol. Biol.* 23:489–499 (1993).

Maniatis, T., et al., in MOLECULAR CLONING: A LABORATORY MANUAL, Cold Spring Harbor Laboratory (1982).

Mathews, H., et al., PCT International Publication No. WO 95/35388, published Dec. 28, 1995.

Melchers, L. S., et al., *Plant Mol. Bio.* 21:583–593 (1993).

Melchers, L. S., et al., *Plant J.* 5:469–480 (1994).

Miki, B. L. A., et al., in PLANT DNA INFECTIOUS AGENTS (Hohn, T., et al., Eds.) Springer-Verlag, Wien, Austria, pp.249–265 (1987).

Mullis, K. B., et al., U.S. Pat. No. 4,683,195, issued Jul. 28, 1987.

Mullis, K. B., U.S. Pat. No. 4,683,202, issued Jul. 28, 1987.

Ni, M., et al., *Plant J.* 7:661–676 (1995).

Ochman, H., et al., in AMPLIFICATION OF FLANKING SEQUENCES BY INVERSE PCR IN PCR PROTOCOLS: A GUIDE TO METHODS AND APPLICATIONS (Innis, et al., Eds.) Academic Press, pp. 291–227 (1990).

Oeller, P. W., et al., *Science* 254:437–439 (1991).

Pearson, W. R., *Methods in Enzymology* 183:63–98 (1990).

Pearson, W. R. and Lipman, D. J., *PNAS* 85:2444–2448 (1988).

Ponstein, A. S., et al., *Plant Physiology* 104:109–118 (1994).

Sachs, A., and Wahle, E., et al., *J. Biol. Chem.* 268:22955–11958 (1993).

Saiki, R. K., et al., *Science* 239:487–491 (1988).

Sambrook, J., et al., in MOLECULAR CLONING: A LABORATORY MANUAL, Cold Spring Harbor Laboratory Press, Vol. 2 (1989).

Sato, T., and Theologis, A., *Proc. Natl. Acad. Sci. USA* 86:6621–6625 (1989).

Schuch, W., *Euphytica.* 79(3):287–291 (1994).

Sheehy, R. E., et al., *J. Bact.* 173:5260–5265 (1991).

Toubart, P., et al., *Plant J.* 3:367–373 (1992).

Van der Straeten, D., et al., *Proc. Natl. Acad. Sci. USA* 87:4859–4863 (1990).

Van Haaren, M. J. J., et al., *Plant Mol. Bio.* 21:625–640 (1993).

Walkerpeach, C. R., et al., *Plant Molecular Biology Manual*, B1:1–19 (1994).

Wang, A. M., et al. in PCR PROTOCOLS: A GUIDE TO METHODS AND APPLICATIONS (M. A. Innis, et al., eds.) Academic Press (1990).

Woloshuk, C. P., et al., *J. Plant Cell* 3:619–628 (1991).

Zhu, Q., et al., *Plant Cell* 7:1681–1689 (1995).

BACKGROUND OF THE INVENTION

In recent years recombinant DNA technology has been used to circumvent many limitations of traditional plant breeding programs. This technology has allowed workers to (i) identify and clone desirable genes (such as, genes expressing products that confer disease and insect resistance (Herreraestrella, et al., 1995), (ii) transfer such genes into plants (Walkerpeach, et al., 1994), and (iii) alter selected plant phenotypes by the expression of such genes (Ferro, et al., 1995; Benfey, et al., 1990; Klee, et al., 1991).

A large number of examples of plant promoters useful for the expression of selected genes in plants are now available (Zhu, et al., 1995; Ni, et al., 1995). These promoters have been used to drive the expression of foreign (or heterologous) genes in plants. In most cases, the 5' non-coding regions of the genes (i.e., regions immediately 5' to the coding region) have been used to generate chimeric genes. These regions are often referred to as promoter or transcriptional regulatory sequences. Promoters useful for the expression of a selected nucleic acid sequence in plants can be derived from plant DNA or from other sources, for example, plant viruses. In most cases, it has been demonstrated that sequences up to about 500–1500 bases allow regulated expression of genes under their control.

Expression of heterologous genes or selected sequences of genes in transgenic plants has typically involved the use of constitutive promoters. Exemplary plant promoters include the following: 35S Cauliflower Mosaic Virus (CaMV 35S), mannopine synthase, and octopine synthase (ocs). Such promoters have been used successfully to direct the expression of heterologous nucleic acid sequences in transformed plant tissue. However, when used to express DNA sequences in transgenic plants these promoters typically provide low level, constitutive expression (i.e., expression in all plant tissue).

Other promoters have been identified that allow tissue specific expression, for example, fruit specific expression, such as the E4 and E8 promoters from tomatoes (Cordes, et al., 1989; Bestwick, et al., 1995). Also, it has been demonstrated that nucleic acid sequences placed under the regulatory control of the 5' non-coding region of the tomato 2AII gene (Van Haaren) are preferentially transcribed in developing fruit tissue. Fruit specific regulation of the kiwifruit actinidin promoter has been reported to be conserved in transgenic petunia plants (Lin, et al., 1993).

SUMMARY OF THE INVENTION

The present invention includes a promoter that allows high-level, tissue specific expression of nucleic acid sequences placed under its regulation. Chimeric genes of the present invention have a DNA sequence encoding a product of interest under the transcriptional control of a dru1 promoter. The DNA sequence is typically heterologous to the promoter and is operably linked to the promoter to enable expression of the product. Exemplary products include, but are not limited to S-adenosylmethionine hydrolase, aminocyclopropane-1-carboxylic acid (ACC) deaminase, ACC oxidase antisense molecule, ACC synthase antisense molecule, ACC oxidase cosuppression molecule, ACC synthase cosuppression molecule, thaumatin, sucrose phosphate synthase and lycopene cyclase.

In one embodiment, the promoters of the present invention can be used to reduce ethylene production in fruit cells.

In another embodiment, the DNA sequence can correspond to a pathogenesis related gene, such as polygalacturonase inhibiting protein (PGIP), glucanase and chitinase.

The promoter of the present invention can be obtained from a gene homologous to a raspberry dru1 gene or from the dru1 raspberry gene itself. An exemplary dru1 promoter sequence is SEQ ID NO:22. Smaller fragments of such a promoter region may be derived from this sequence, where the smaller fragments are effective to regulate expression of a DNA sequence under their control.

The present invention also includes the use of any of the above chimeric genes to generate a plant transformation vector. Such vectors can be used in any plant cell transformation method, including, Agrobacterium-based methods, electroporation, microinjection, and microprojectile bombardment. These vectors may form part of a plant transformation kit. Other components of the kit may include, but are not limited to, reagents useful for plant cell transformation.

In another embodiment, the present invention includes a plant cell, plant tissue, transgenic plant, fruit cell, whole fruit, seeds or calli containing any of the above-described chimeric genes.

In another aspect of the present invention, the promoters described herein are employed in a method for modifying ripening fruit of a fruit bearing plant. In this method, transgenic plants containing the chimeric gene of the present invention are grown to produce a transgenic plant bearing fruit. In this embodiment, the chimeric gene encodes a product capable of reducing ethylene biosynthesis when expressed in plant cells (e.g., S-adenosylmethionine hydrolase, aminocyclopropane-1-carboxylic acid (ACC) deaminase, ACC oxidase antisense molecule, ACC synthase antisense molecule, ACC oxidase cosuppression molecule, ACC synthase cosuppression molecule). Fruit produced by these transgenic plants have a modified ripening phenotype. A modified ripening phenotype typically refers to an alteration of the rate of ripening of a transgenic fruit relative to corresponding (i.e., non-transgenic) wild-type fruit.

Further, the invention includes a method for producing a transgenic fruit-bearing plant. In his method the chimeric gene of the present invention, typically carried in an expression vector allowing selection in plant cells, is introduced into progenitor cells of selected plant. These progenitor cells are then grown to produce a transgenic plant bearing fruit. The method may further comprise isolation of a dru1 promoter by the following steps:

(i) selecting a probe DNA molecule containing a sequence homologous to a region of raspberry dru1 gene DNA, (ii) contacting the probe with a plurality of target DNA molecules derived from the genome of a selected fruit-bearing plant under conditions favoring specific hybridization between the probe molecule and a target molecule homologous to the probe molecule, (iii) identifying a target molecule having a DNA sequence homologous to the raspberry dru1 gene, and (iv) isolating promoter sequences associated with the target molecule.

In addition, the present invention includes isolation of a dru1 promoter by the steps just described.

The chimeric genes, vectors, products and methods of the present invention can also be produced using dru2 promoter sequences identified essentially as described herein for dru1.

In another aspect of the present invention, sequences useful for the stabilization of mRNA can be derived from dru1 gene sequences and used in the construction of chimeric genes.

These and other objects and features of the invention will be more fully appreciated when the following detailed description of the invention is read in conjunction with the accompanying drawings.

BRIEF DESCRIPTION OF THE FIGURES

In FIG. 2a, in the first set of constructs in the strand labeled "mRNA", the sequence at the 3' end corresponds to SEQ ID NO:23; in the complementary strand with the subheading "dTRANDOM primer", the sequence at the 5' end corresponds to SEQ ID NO:2. In the second set of constructs, in the strand labeled "1st strand cDNA", the 3' end corresponds to SEQ ID NO:24 and the 5' end corresponds to SEQ ID NO:2; in the complementary strand labeled "1st round PCR", the 5' end corresponds to SEQ ID NO:4 and the 3' end corresponds to SEQ ID NO:25. In the third set of constructs, in the strand labeled "1st round PCR", the 5' end corresponds to SEQ ID NO:4 and the 3' end corresponds to SEQ ID NO:25; in the complementary strand labeled "2nd round PCR", the 3' end corresponds to SEQ ID NO:26 and the 5' end corresponds to SEQ ID NO:5. In the last set of constructs, the sequence shown corresponds to SEQ ID NO:27.

FIGS. 3A and 3B present the genomic DNA sequence of the dru1 gene (SEQ ID NO:12) and the corresponding protein (SEQ ID NO:13). Indicated in the figures are a CAAT box, TATA box, ATG start codon, two exons, an intron, splicing sites, a stop codon and poly-adenylation sites.

DETAILED DESCRIPTION OF THE INVENTION

I. Definitions

Figure 1:
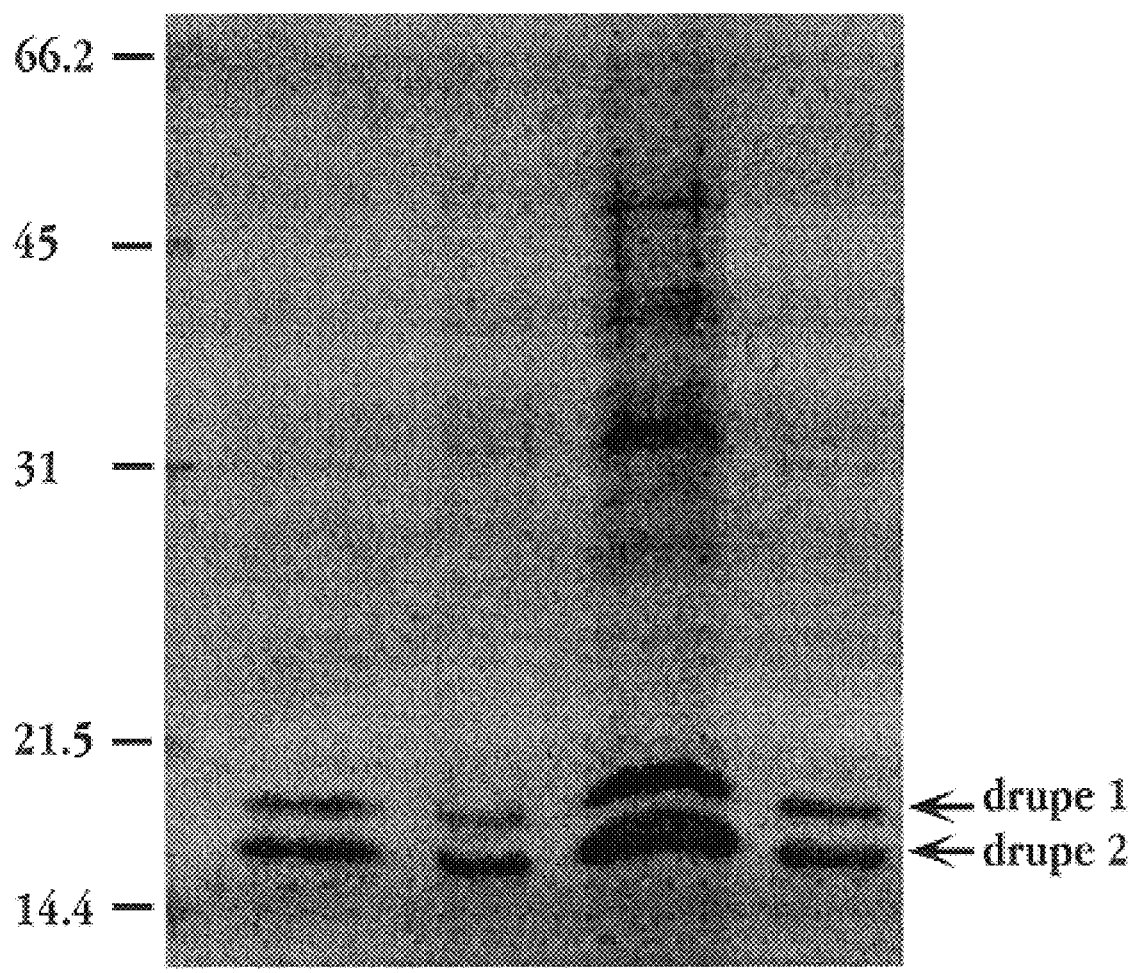
FIG. 1 presents representative results of polyacrylamide gel electrophoretic analysis of raspberry drupelet proteins.

A "chimeric gene," in the context of the present invention, typically comprises a promoter sequence operably linked to "heterologous" DNA sequences, i.e., DNA sequences that encode a gene product not normally contiguous or associated with the promoter (e.g., a dru1 promoter adjacent DNA sequences encoding S-adenosylmethionine cleaving enzyme).

"dru1 homologous genes" are defined as genes that have at least about 55% or preferably 80% global sequence homology, that is, sequence identity over a length of the polynucleotide sequence to the raspberry dru1 polynucleotide sequences disclosed herein (e.g., SEQ ID NO:10).

"Sequence homology" is determined essentially as follows. Two polynucleotide sequences of the same length (preferably, corresponding to the coding sequences of the gene) are considered to be homologous to one another, if, when they are aligned using the ALIGN program, over 55% or preferably 80% of the nucleic acids in the highest scoring alignment are identically aligned using a ktup of 1, the default parameters and the default PAM matrix (Dayhoff, 1972).

The ALIGN program is found in the FASTA version 1.7 suite of sequence comparison programs (Pearson and Lipman, 1988; Pearson, 1990; program available from William R. Pearson, Department of Biological Chemistry, Box 440, Jordan Hall, Charlottesville, Va.).

Two nucleic acid fragments are considered to be "selectively hybridizable" to a polynucleotide derived from a dru1 gene, if they are capable of specifically hybridizing to the coding sequences of the raspberry dru1 gene or a variant thereof or of specifically priming a polymerase chain amplification reaction: (i) under typical hybridization and wash conditions, as described, for example, in Maniatis, et al., (1982), pages 320–328, and 382–389. Examples of such hybridization conditions are also given in Examples 8 and 9; (ii) using reduced stringency wash conditions that allow at most about 25–30% basepair mismatches, for example: 2× SSC, 0.1% SDS, room temperature twice, 30 minutes each; then 2× SSC, 0.1% SDS, 37° C. once, 30 minutes; then 2× SSC room temperature twice, 10 minutes each, or (iii) selecting primers for use in typical polymerase chain reactions (PCR) under standard conditions (for example, in Saiki, et al., 1988), which result in specific amplification of sequences of dru1 or its variants.

Preferably, highly homologous nucleic acid strands contain less than 20–40% basepair mismatches, even more preferably less than 5–20% basepair mismatches. These degrees of homology can be selected by using wash conditions of appropriate stringency for identification of clones from gene libraries (or other sources of genetic material), as is well known in the art.

A "dru1 encoded polypeptide" is defined herein as any polypeptide homologous to a dru1 encoded polypeptide. In one embodiment, a polypeptide is homologous to a dru1 encoded polypeptide if it is encoded by nucleic acid that selectively hybridizes to sequences of dru1 or its variants.

In another embodiment, a polypeptide is homologous to a dru1 encoded polypeptide if it is encoded by dru1 or its variants, as defined above, polypeptides of this group are typically larger than 15, preferable 25, or more preferable 35, contiguous amino acids. Further, for polypeptides longer than about 60 amino acids, sequence comparisons for the purpose of determining "polypeptide homology" are performed using the local alignment program LALIGN. The polypeptide sequence is compared against the dru1 amino acid sequence or any of its variants, as defined above, using the LALIGN program with a ktup of 1, default parameters and the default PAM.

Any polypeptide with an optimal alignment longer than 60 amino acids and greater than 55% or preferably 80% of identically aligned amino acids is considered to be a "homologous polypeptide." The LALIGN program is found in the FASTA version 1.7 suite of sequence comparison programs (Pearson and Lipman, 1988; Pearson, 1990; program available from William R. Pearson, Department of Biological Chemistry, Box 440, Jordan Hall, Charlottesville, Va.).

A polynucleotide is "derived from" dru1 if it has the same or substantially the same basepair sequence as a region of the dru1 protein coding sequence, cDNA of dru1 or complements thereof, or if it displays homology as noted above.

A polypeptide or polypeptide "fragment" is "derived from" dru1 if it is (i) encoded by a dru1 gene, or (ii) displays homology to dru1 encoded polypeptides as noted above.

In the context of the present invention, the phrase "nucleic acid sequences," when referring to sequences which encode a protein, polypeptide, or peptide, is meant to include degenerative nucleic acid sequences which encode homologous protein, polypeptide or peptide sequences as well as the disclosed sequence.

A "modified ripening" phenotype typically refers to an alteration of the rate of ripening of a transgenic fruit relative to corresponding wild-type fruit, such as, for example, delayed ripening fruit (i.e., ripening takes longer than corresponding wild-type fruit) or suspension of the fruit's ability to complete the ripening process.

A "product" encoded by a DNA molecule includes, for example, an RNA molecule or a polypeptide.

II. dru1 Protein Identification, Purification and Sequence Determination

The present invention relates to the cloning of a gene expressed at very high levels in ripening fruit, exemplified by the dru1 gene from raspberries. Expression directed by the dru1 promoter described herein is fruit specific and active during fruit ripening.

Protein(s) such as those produced by raspberry are typically analyzed by gel electrophoresis. A coomassie blue-stained SDS polyacrylamide gel of soluble drupelet proteins is shown in FIG. 1 (Example 1). Two highly abundant proteins isolable from raspberries are observed at approximately 17 and 15 kd, and are referred to herein as drupe1 and drupe2, respectively. The amount of drupe1 and drupe2 relative to the total amount of soluble protein can be determined, for example, by scanning densitometry. Scanning densitometry analysis of the gel illustrated in FIG. 1 indicates that drupe1 and drupe2 comprise approximately 23 and 37%, respectively, of the total soluble protein in raspberry drupelets. As a result of this determination (i.e., the high levels of drupe1 and drupe2), purification and sequencing of drupe1 and drupe2 can be carried out, for example, by using a direct western blot approach.

In carrying out a western blot analysis, total drupelet proteins are western blotted to PDVF membrane (Example 1) and the regions corresponding to drupe1 and drupe2 are subjected to N-terminal amino acid sequence analysis. The drupe1 sample yields a thirty amino acid N-terminal sequence (Example 1). The amino terminal drupe1 sequence is presented herein as SEQ ID NO:1.

III. Cloning dru1 Encoding Sequences

A. RT-PCR and Cloning of a dru1 cDNA Clone

Figure 2A:
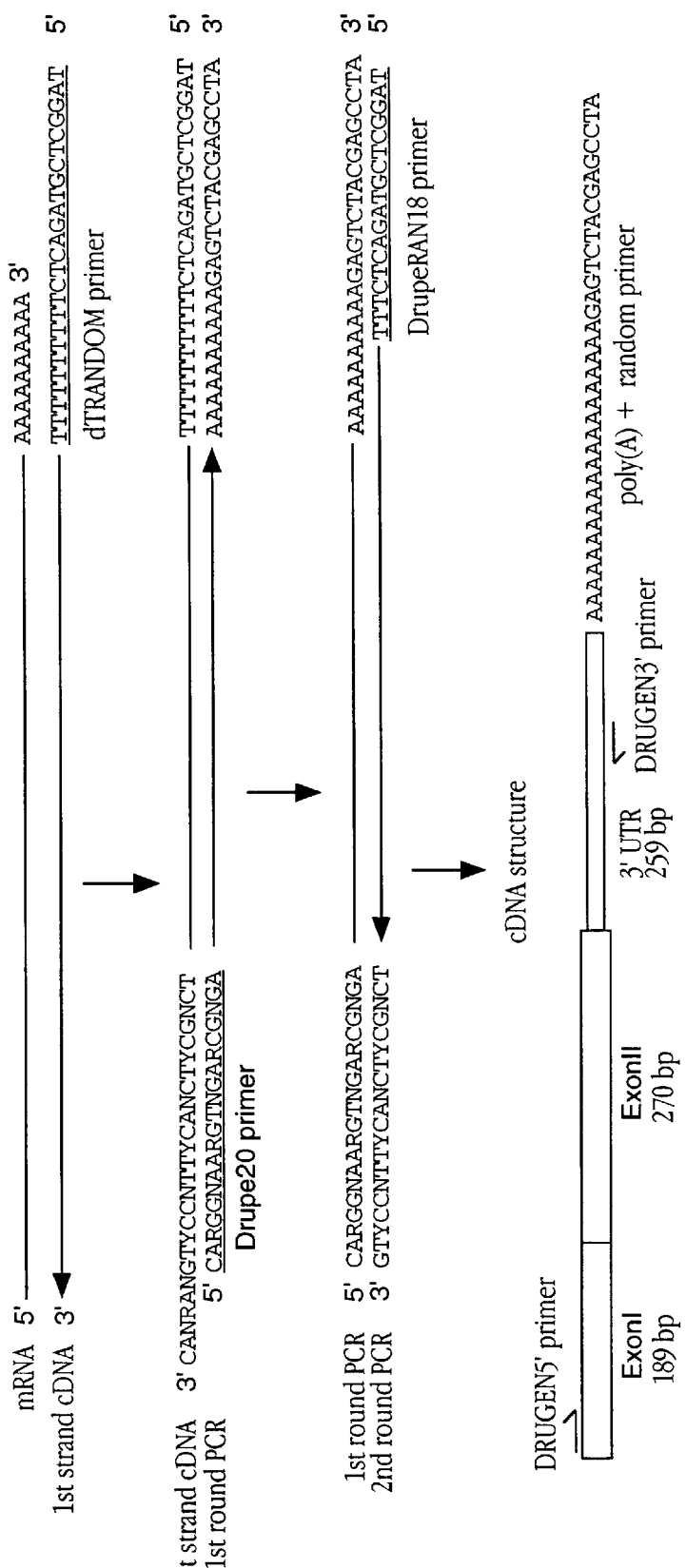
FIGS. 2A and 2B schematically represent the Reverse Transcriptase-Polymerase Chain Reaction (RT-PCR; Kawasaki, et al., 1989; Wang, et al., 1990) cloning of the raspberry dru1 gene.
Figure 2B:
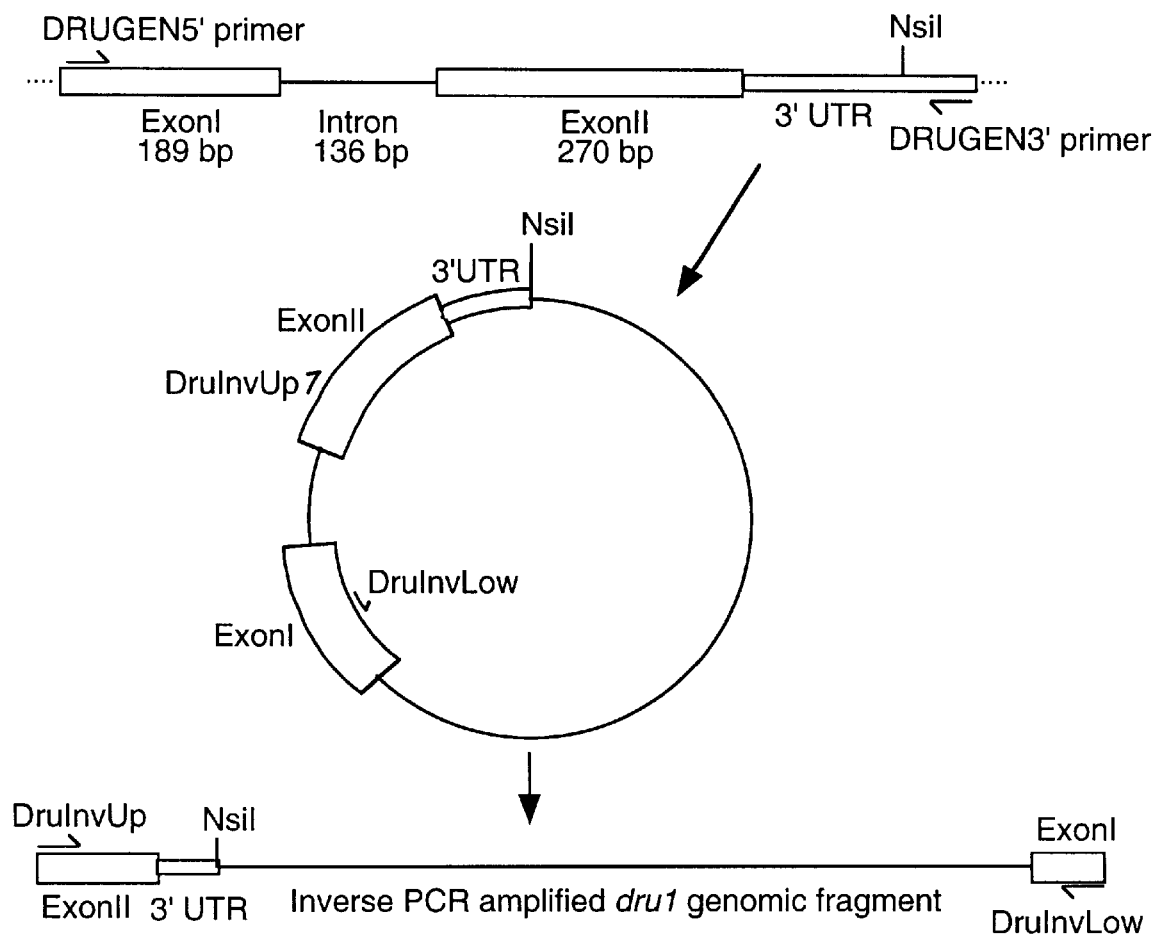

The entire procedure for cloning dru1, from cDNA synthesis to inverse PCR of a genomic copy of the gene, is shown schematically in FIGS. 2A and 2B.

In carrying out the cloning procedure, mature green raspberry drupelet mRNA is prepared as described in Example 2 and used as template in a cDNA synthesis reaction. The reaction is primed using the dTRANDOM primer shown in FIGS. 2A and 2B. The resulting cDNA (Example 2) is subjected to a standard PCR reaction using primers corresponding to a portion of the dTRANDOM primer and a 512-fold degenerate primer (Drupe 20) based on the drupe1 amino terminal sequence (Example 3).

The PCR amplification products are then analyzed. Products from the above PCR reaction include a 710 bp product that is agarose gel purified and subcloned into pCRII (Example 3). Subsequent sequence analysis of several of these clones allows identification of those clones whose sequence encodes a protein matching the amino terminal sequence of drupe1.

A. Inverse PCR Cloning of a Genomic Copy of the dru1 Gene

In this approach to cloning the dru1 gene, genomic raspberry DNA is used in a PCR reaction using primers internal to the cDNA sequence obtained as described above (Example 4). This reaction produces a genomic clone of the dru1 gene containing most of the protein coding region. A single intron was identified from the subsequent sequence analysis of this clone (FIG. 3B). An inverse PCR strategy may be employed to characterize and sequence the 5' region of the gene containing the dru1 promoter (Example 5). FIGS. 2A and 2B show schematically how this may be accomplished.

In characterizing the 5' flanking region of dru1 genomic DNA utilizing inverse PCR techniques, raspberry genomic DNA is digested with NsiI and ligated under dilute conditions to allow circularization of the restriction fragments. The ligated DNA is then subjected to PCR amplification using primers internal to the dru1 coding sequence and oriented in opposite directions from each other. This produces a PCR reaction product containing part of the first exon and 1.35 kb of the promoter. Subsequent sequence analysis of this clone in combination with sequence information from the previously described clones produces the complete dru1 sequence (SEQ ID NO:12).

B. Sequence Determination and Evaluation of Gene Expression Patterns

The dru1 gene (SEQ ID NO:12) encodes a protein with the predicted amino acid sequence presented as SEQ ID NO:13. The predicted molecular weight for this protein is 17,088, which agrees closely with the 17 kd molecular weight determined by gel electrophoresis (see FIG. 1) of total drupelet protein. The dru1 protein is relatively acidic with a predicted pI of 4.8. Nucleic acid and protein homology searches of the current sequence databases can be carried out to look for significant matches. For dru1, nucleic acid and protein homology searches of the current sequence databases produced no significant matches. This result supports the original observation made with the amino terminal sequence of the protein that drupe1 is a novel protein.

The gene expression pattern of dru1 can be also be evaluated at the RNA and protein levels to confirm the tissue specificity of the promoter. Northern dot blots, FIGS. 6 and 7, of total RNA from raspberry leaf and receptacles at different ripening stages indicate a tissue and stage specific gene expression pattern. This can be confirmed by comparison of northern blots of total RNA from various other plant tissues. The tissue and stage specific gene expression pattern of dru1 was confirmed on northern blots of total RNA from leaf, receptacles, and drupelets (see FIGS. 6 and 7). In both cases, no dru1 expression is observed in leaf RNA. The RNA expression pattern in receptacles is temporally regulated while in drupelets it is fully expressed at the two stages (i.e., green and ripe) analyzed.

Figure 8:
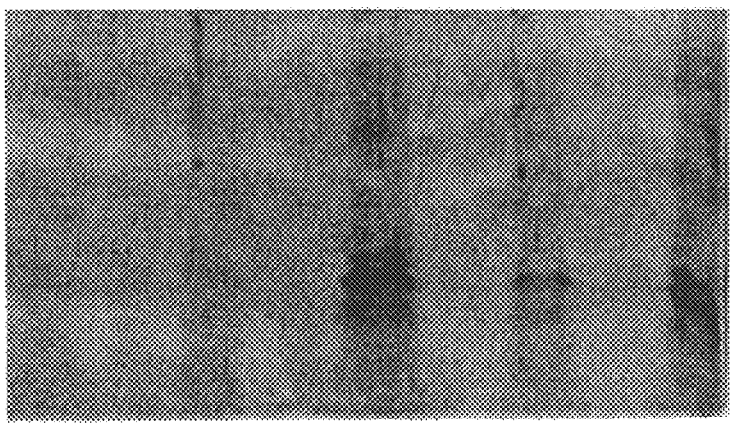
FIG. 8 shows the results of polyacrylamide gel electrophoretic analysis of raspberry drupelet proteins obtained from drupelets at various stages of ripening.

A protein gel of drupelet lysates from different ripening stages can also be carried out to further support stage specific expression of dru1. As illustrated in FIG. 8, electrophoretic analysis of raspberry drupelet proteins obtained from drupelets at various stages of ripening (i.e., green, mature green, breaker, orange, and ripe) further supports a stage specific expression pattern in drupelets (FIG. 8).

C. Promoter Isolation and Construction of Chimeric Genes

Characterization of the dru1 genomic clone allows isolation of the dru1 promoter. The promoter can then be used to regulate expression of heterologous genes. An exemplary dru1 promoter has the sequence presented as SEQ ID NO:22.

In support of the present invention, two exemplary chimeric genes containing a dru1 promoter sequence operably linked to a heterologous DNA sequence, were constructed, dru1pro:SAMase and dru1pro:PGIP (Example 7). S-adenosylmethionine hydrolase (SAMase) and polygalacturonase inhibiting protein (PGIP) confer ethylene control and fungal resistance, respectively, in transgenic plants. Both proteins have been predicted to function more efficiently if expressed (i) in high levels and (ii) in a tissue specific manner. Accordingly, the dru1 promoter represents an ideal promoter to satisfy this objective.

Figure 9:
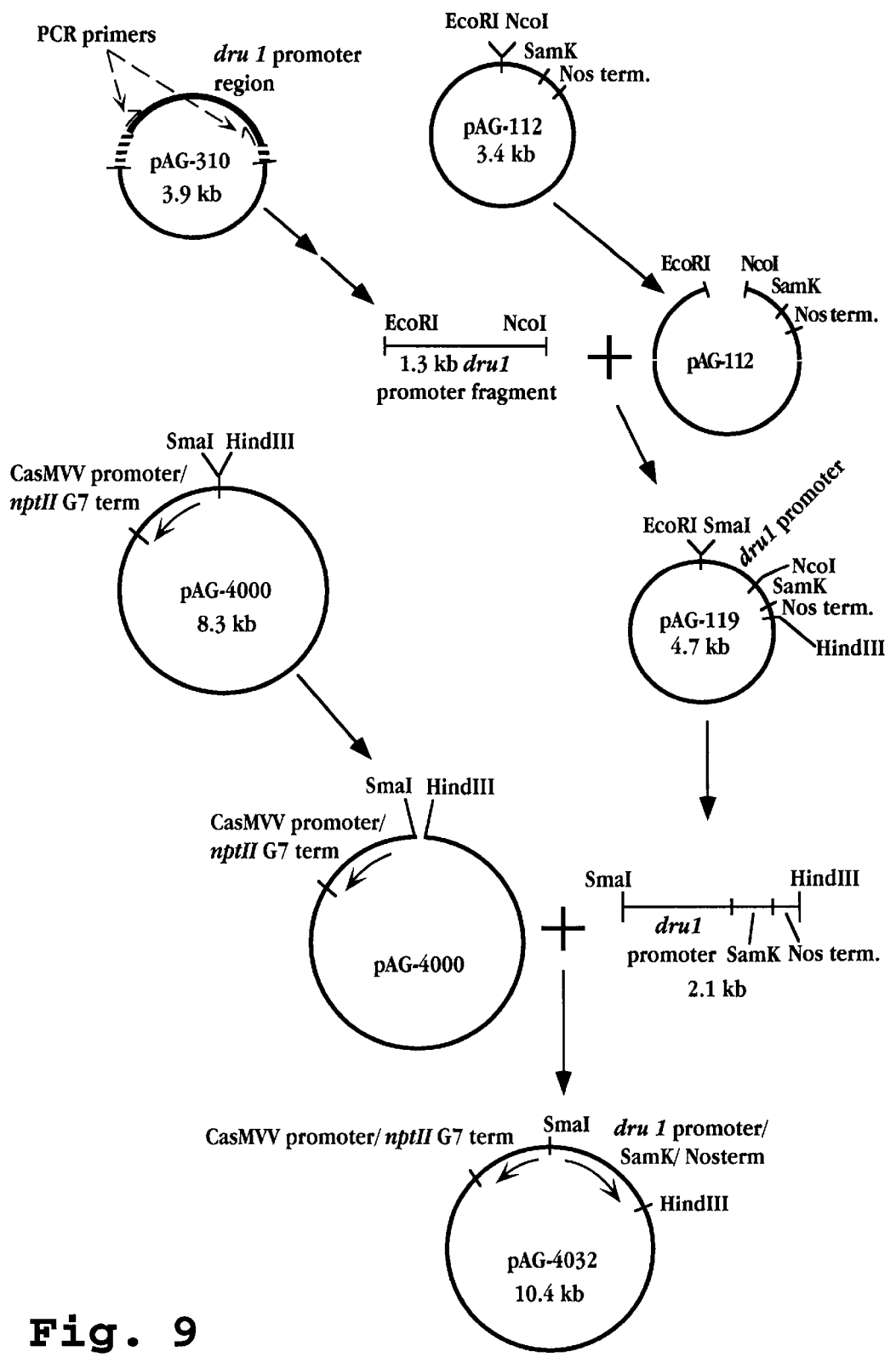
FIG. 9 presents a schematic description of the details of the vector construction for pAG-4032.
Figure 10:
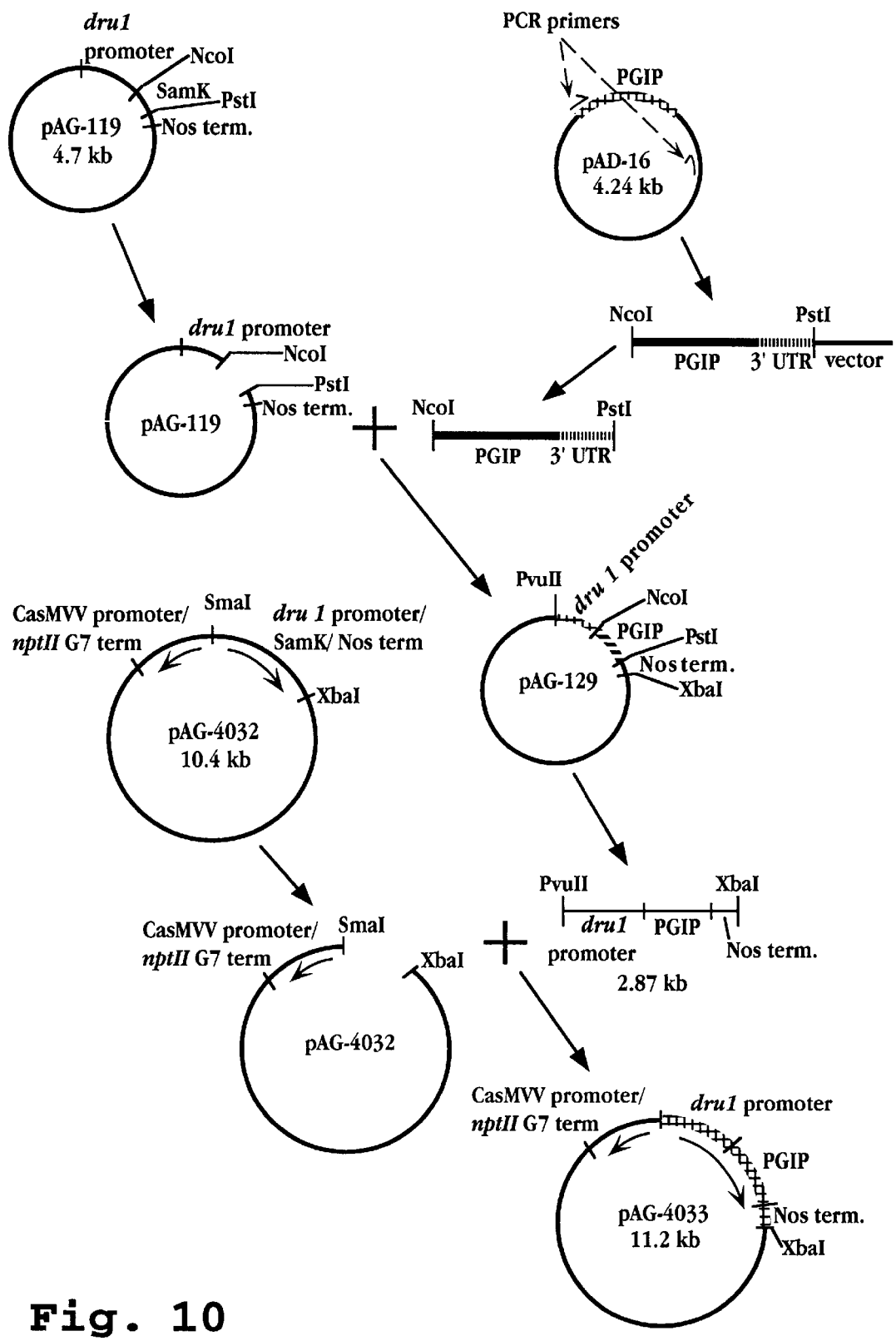
FIG. 10 presents a schematic description of the details of the vector construction for pAG-4033.

Construction of Agrobacterium binary vectors, pAG-4032 and pAG-4033, containing the two representative chimeric genes described above, can be performed as described in Example 7 (schematically represented in FIGS. 9 and 10, dru1pro:SAMase and dru1pro:PGIP, respectively).

IV. Stabilization of mRNA Using dru1 3' Untranslated Sequences

The level of both protein and mRNA expression of dru1 is very high. Although not wishing to be bound by any particular mechanism for the observations described herein, there are several possible mechanisms that may contribute to such high level protein and mRNA expression. The first mechanistic possibility is that the dru1 promoter is a strong promoter. Data supporting this mechanism for protein and mRNA expression is discussed above.

A second possibility is that the dru1 mRNA may have a low turnover rate, resulting in an accumulation of dru1 mRNA and subsequent higher levels of translation. In considering this mechanistic possibility, the dru1 mRNA has a relatively long untranslated 3' end (dru1T). This region may confer enhanced mRNA stability, thus making this region useful as a superior transcriptional stop signal. mRNA stability has been correlated with certain 3'-untranslated sequences in other non-plant systems (Sachs and Wahle, 1993; Li and Hunt, 1995).

To examine the function of the dru1 3'-untranslated sequences, an E8 (Bestwick, et al., 1995; Cordes, et al., 1989) promoter can be functionally attached to a DNA fragment encoding the SAMase protein which has the dru1 3'-untranslated sequences (e.g., from about nucleotide 1955 through 2213 of SEQ ID NO:12) at the 3' end of the chimeric gene. This chimeric gene is expressed in tomato. The stability of mRNA produced by this construct is compared to the stability of mRNA produced by a similar construct having typical termination sequences, namely the nopaline synthase termination signal (nosT, GENBANK #TIPOST37; Bevan, et al., 1983; Depicker, et al., 1982) and the Agrobacterium gene 7 signal (Dhaese, et al., 1983).

Figure 11:
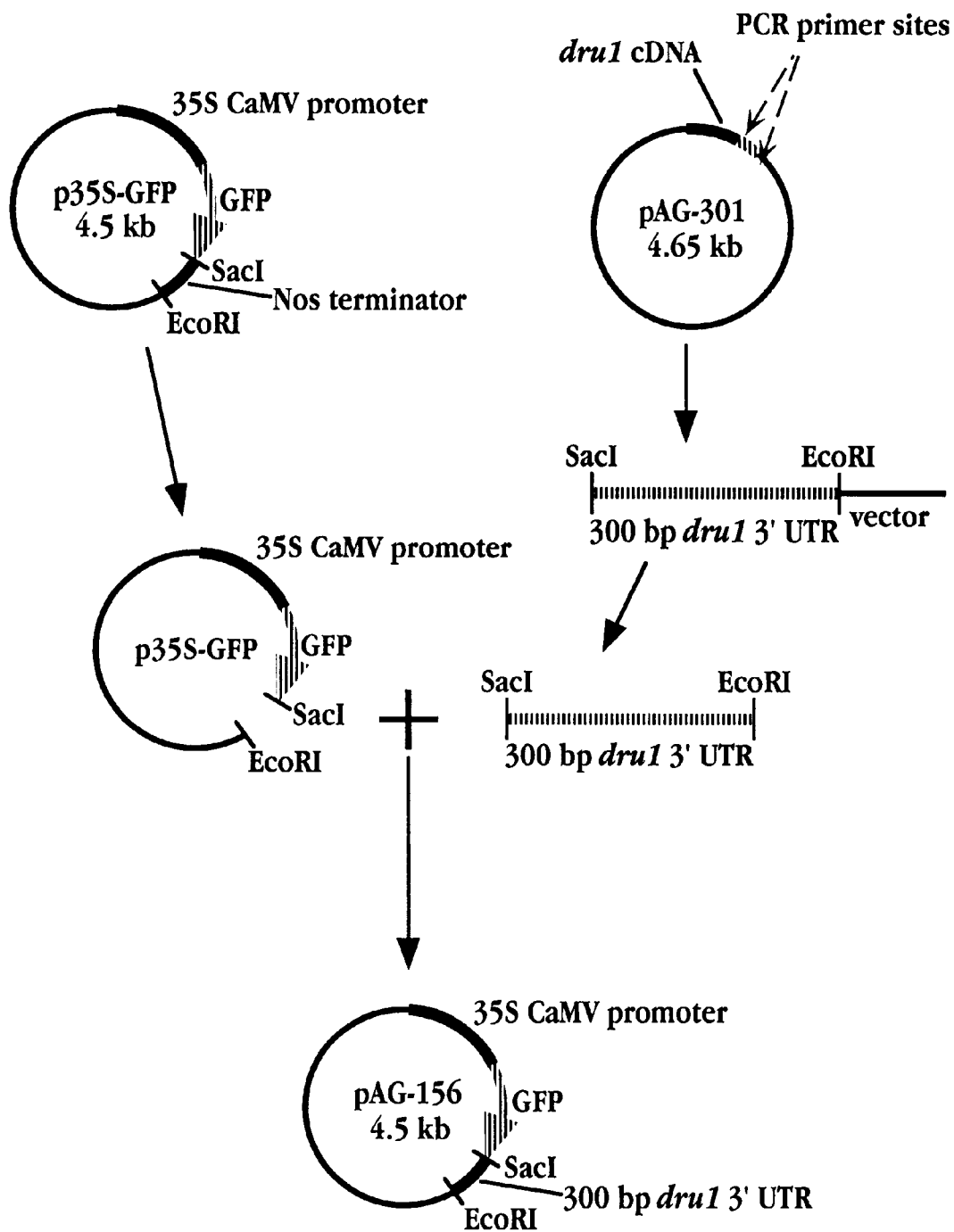
FIG. 11 presents a schematic description of the details of construction of the GFP:dru1T plasmid, pAG-156.

In addition to the above approach, FIG. 11 illustrates a cloning strategy for using an exemplary marker gene, the green fluorescent protein (GFP) (Chalfie, et al., 1994), combined with either the nos termination signals (nosT) or the dru1 termination signals (dru1T). Such reporter plasmids can be used in transient expression studies to determine the relative stabilities of control termination signals (such as, nosT) versus the GFP:dru1T chimera (indicated in FIG. 11 as plasmid pAG-156). A region of the dru1 gene for constructing reporter plasmids such as the GFP:dru1T chimera, and which may be useful as a termination signal, is from about nucleotides 1966 through 2213 as presented in SEQ ID NO:12. Transient expression experiments carried out in support of the invention with the GFP:nosT and GFP:dru1T plasmids demonstrate the usefulness of the dru1 termination signal (dru1T) as a mRNA stabilizing element.

V. Identification of Plant dru1 Promoters

The present invention provides for the use of dru1 promoters from species other than raspberry. Such promoters are useful for the generation of vector constructs containing heterologous genes. Southern blot experiments are used to demonstrate the presence of DNA molecules having significant sequence identity (i.e., typically greater than 55%, more preferably greater than 80% identity using standard sequence comparison programs) with the raspberry dru1 gene in, for example, strawberry, peach or plum. Similar Southern blot analyses may be performed on other fruit-bearing plants to identify additional dru1 genes.

A Southern blot analysis used herein is detailed in Example 8. dru1 homologues are identified in a Southern blot of the genomic DNA of the plants listed above probed with a labelled DNA fragment containing the coding sequence of the raspberry dru1 gene.

The probe is selected to contain the coding sequence of dru1, rather than the promoter sequence, because coding sequences are typically more conserved from species to species than are promoter sequences. In the experiments detailed in Examples 8 and 9, probe molecules are generated from raspberry genomic DNA using primer-specific amplification (Mullis, 1987; Mullis, et al., 1987). The oligonucleotide primers are selected such that the amplified region includes the entire coding sequence of the raspberry dru1 gene. Primers may also be selected to amplify only a selected region of the raspberry dru1 gene.

Alternatively, a probe can be made by isolating restriction-digest fragments containing the sequence of interest from plasmid DNA.

The probe is labeled with a detectable moiety to enable subsequent identification of homologous target molecules. Exemplary labeling moieties include radioactive nucleotides, such as $^{32}$P-labeled nucleotides, digoxygenin-labeled nucleotides, biotinylated nucleotides, and the like, available from commercial sources.

In the case of primer-amplified probes, labeled nucleotides may be directly incorporated into the probe during the amplification process. Probe molecules derived from DNA that has already been isolated, such as restriction-digest fragments from plasmid DNA, are typically end-labeled (Ausubel, et al., 1992).

Target molecules, such as HindIII DNA fragments from the genomes of the above-listed plants, are electrophoresed on a gel, blotted, and immobilized onto a nylon or nitrocellulose filter. Labeled probe molecules are then contacted with the target molecules under conditions favoring specific hybridization between the probe molecules and target molecules homologous to the probe molecules (Maniatis, et al., 1982; Sambrook, et al., 1989; Ausubel, et al., 1992).

Conditions favoring specific hybridization are referred to as moderately to highly stringent, and are affected primarily by the salt concentration and temperature of the wash buffer (Ausubel, et al., 1992; Sambrook, et al., 1989). Conditions such as those used in the final wash in Example 9 are typically classified as moderately stringent, due to the low salt concentration, and are expected to preserve only specific hybridization interactions, allowing the identification and isolation of homologous genes in different plant species.

Following contacting, hybridization, and washing, target molecules with sequences homologous to the probe are identified by detecting the label on the probe. The label may be detected directly, for example, as in a radioactive label detected on autoradiograms, or it may be detected with a secondary moiety, for example, fluorescently-labeled streptavidin binding to a biotinylated probe.

Following the identification of plants containing dru1 genes, the DNA containing the desired genes, including the promoter regions, may be isolated from the respective species, by, for example, the methods described herein for the isolation of the raspberry dru1 gene.

Typically, a library of interest (e.g., genomic or cDNA) is screened with a probe containing sequences corresponding to the coding sequence of a known dru1 gene, such as the raspberry dru1 gene (Example 9). The screening is done using known methods (Ausubel, et al., 1992; Sambrook, et al., 1989), essentially as described above.

Positive plaques or colonies are isolated, and the insert DNA is sequenced and compared to known dru1 sequences. Clones containing inserts with sequences corresponding to genes homologous to raspberry dru1 are identified and, if necessary, used to obtain additional clones until the promoter region of interest is isolated.

Variants of the dru1 promoter may be isolated from different raspberry cultivars and from other plants by the methods described above. A reporter gene, such as GUS (β-glucuronidase), can be used to test tissue and/or stage specific (e.g., stages of fruit ripening) regulatable expression from such promoters. Expression of GUS protein can be easily measured by fluorometric, spectrophotometric or histochemical assays (Jefferson, 1987a, 1987b).

Further, using chimeric genes containing dru1 promotor sequences operably linked to reporter gene sequences, DNA sequences corresponding to regulatory domains can be identified using, for example, deletion analysis (Benfey, et al., 1990). For example, the dru1 promoter sequence presented as SEQ ID NO:22 can be functionally linked to the GUS reporter gene. Deletion analysis can then be carried out by standard methods (Ausubel, et al., 1992; Maniatis, et al., 1982; Sambrook, et al.). Alternatively, regions of the dru1 promoter sequence can be amplified using sequence-specific primers in PCR. These amplified fragments can then be inserted 5' to the GUS coding sequences and the resulting expression patterns evaluated.

VI. Plant Transformation and the Generation of Transgenic Plants

A. The Vectors of the Present Invention

Plant transformation vectors, containing dru1 promoter/ transcription-regulatory sequences, are constructed according to methods known in the art (see, for example, Houck and Pear, 1990, and Becker, et al., 1992).

The present invention provides vectors suitable for the transformation of plants. The vectors, chimeric genes and DNA constructs of the present invention are also useful for the expression of heterologous genes. Transgenic plants, and their fruit products, carrying the chimeric genes of the present invention, may be a useful source of recombinantly-expressed material.

In one embodiment, the chimeric genes of the present invention have two components: (i) a promoter derived from a dru1 gene, and (ii) a heterologous DNA sequence encoding a desirable product.

The vectors of the present invention may be constructed to carry an expression cassette containing an insertion site for DNA coding sequences of interest. The transcription of such inserted DNA is then under the control of a suitable dru1 promoter (i.e., raspberry dru1 gene promoter or homologs thereof).

Such expression cassettes may have single or multiple transcription termination signals at the coding-3'-end of the DNA sequence being expressed. Such 3' sequences may include transcription termination sequences derived from the 3' non-coding region of the dru1 gene encoded mRNA. The expression cassette may also include, for example, DNA sequences encoding (i) a leader sequence (e.g., to allow secretion or vacuolar targeting), and (ii) translation termination signals.

Further, the vectors of the present invention may include selectable markers for use in plant cells (such as, the nptII kanamycin resistance gene). The vectors may also include sequences that allow their selection and propagation in a secondary host, such as, sequences containing an origin of replication and a selectable marker. Typical secondary hosts include bacteria and yeast. In one embodiment, the secondary host is *Escherichia coli*, the origin of replication is a colE1-type, and the selectable marker is a gene encoding ampicillin resistance. Such sequences are well known in the art and are commercially available as well (e.g., Clontech, Palo Alto, Calif.; Stratagene, La Jolla, Calif.).

The vectors of the present invention may also be modified to intermediate plant transformation plasmids that contain a region of homology to an *Agrobacterium tumefaciens* vector, a T-DNA border region from *Agrobacterium tumefaciens*, and chimeric genes or expression cassettes (described above). Further, the vectors of the invention may comprise a disarmed plant tumor inducing plasmid of *Agrobacterium tumefaciens*. Other suitable vectors may be constructed using the promoters of the present invention and standard plant transformation vectors, which are available both commercially (Clontech, Palo Alto, Calif.) and from academic sources (Waksman Institute, Rutgers, The State University of New Jersey, Piscataway, N.J.).

The vectors of the present invention are useful for tissue and/or stage-specific expression of nucleic acid coding sequences in plant cells. For example, a selected peptide or polypeptide coding sequence can be inserted in an expression cassette of a vector of the present invention. The vector is then transformed into host cells, the host cells cultured under conditions to allow the expression of the protein coding sequences, and the expressed peptide or polypeptide isolated from the cells. Transformed progenitor cells can also be used to produce transgenic plants bearing fruit.

In one aspect of the invention, fruit produced by such transgenic plants has a reduced level of ethylene synthesis by the fruit. The fruit then demonstrates a modified ripening phenotype.

The vectors, chimeric genes and DNA constructs of the present invention can be sold individually or in kits for use in plant cell transformation and the subsequent generation of transgenic plants.

B. Heterologous Genes

The methods and results described herein demonstrate the ability to provide tissue and/or stage specific regulation of gene expression in transgenic plants. The tissue and/or stage-specific promoters of the present invention include a region of DNA that regulates transcription of the immediately adjacent (downstream) gene to a specific plant tissue. According to methods of the present invention, heterologous genes are linked to the promoters of the present invention. Exemplary heterologous gene for the transformation of plants include genes whose products are effective to reduce ethylene biosynthesis in specific tissues of those plants, e.g.

the fruits. Some of these genes, including AdoMetase, are discussed above.

Other genes of interest that could be used in conjunction with the dru1 promoter include, but are not limited to, the following: other ripening modification genes, in addition to AdoMetase, such as, aminocyclopropane-1-carboxylic acid (ACC) deaminase (Klee, et al., 1991; Sheehy, et al., 1991), which degrades precursors of ethylene biosynthesis; ripening modification through the use of gene inactivation methods including antisense or cosuppression affecting genes of the ethylene biosynthetic pathway such as the genes encoding ACC synthase (Sato and Theologis, 1989) or ACC oxidase (Hamilton, et al., 1990). Further, the usefulness of genes involved in conferring fungal resistance (e.g., the polygalacturonase inhibiting protein (PGIP) from *Phaseolus vulgaris* (Toubart, et al., 1992) and modified forms of plant glucanase, chitinase and other pathogenesis related (PR) genes (Melchers, et al., 1993, 1994; Ponstein, et al., 1994; Woloshuk, et al., 1991) would be improved when used with a high-level, fruit-specific promoter such as dru1.

In addition, antisense or cosuppression genes encoding proteins responsible for degradative processes in the fruit may also be used in conjunction with the promoters of the present invention. Examples of genes of this type include polygalacturonase, cellulase, and pectin methyl esterase (Schuch, 1994). Use of the promoters of the present invention targets inhibition of the specific degradation process to only ripening fruit.

Other gene products which may be useful to express using the promoters of the present invention include genes encoding (i) flavor (e.g., thaumatin; GENBANK) or color modification (e.g., products that modify lycopene synthesis, for example, arabidopsis lycopene cyclase; GENBANK), (ii) enzymes or other catalytic products (such as, ribozymes or catalytic antibodies) that modify plant cell processes, (iii) gene products that affect ethylene production, such as antisense molecules, enzymes that degrade precursors of ethylene biosynthesis, catalytic products or cosuppression molecules, (iv) alternative fungal control genes, and (v) sucrose accumulating genes, such as the sucrose phosphate synthase gene (GENBANK) from corn.

Further, it is useful to restrict expression of some genes to specific tissues, such as the fruit—for example, any gene that would be deleterious to the plant if it were expressed constitutively. Such genes would include genes which encoded degradative enzymes that deplete necessary metabolites. Derivatives of the dru1 promoter region can be used as on/off switches for the tissue and/or stagespecific expression of genes whose expression is under their control.

C. Methods of Transforming Plants

A number of methods, in addition to Agrobacterium-based methods, may be employed to elicit transformation of plant progenitor cells, such as electroporation, microinjection, and microprojectile bombardment. These methods are well known in the art (Comai and Coning, 1993; Klein, et al., 1988; Miki, et al., 1987; Bellini, et al., 1989) and provide the means to introduce selected DNA into plant genomes: such DNA may include a DNA cassette which consists of a dru1 gene promoter functionally adjacent to heterologous sequences encoding a desired product, for example, AdoMetase coding sequences. Transformants and resulting transgenic cells and transgenic plants are identified and evaluated by standard methods (Mathews, et al., 1995).

D. Expression in Heterologous Plant Systems

Experiments performed in support of the present invention demonstrate the versatility of the chimeric gene constructs of the invention. The vector constructs of the present invention can be used for transformation and expression of heterologous sequences in transgenic plants independent of the original plant source for the promoter sequence. Further, the expression mediated by the promoter appears to be tissue and/or stage-specific even in heterologous plants. Accordingly, the vectors, chimeric genes and DNA constructs of the present invention are useful for transformation of species of fruit-bearing plants, where such plants are different species than the plant source of the promoter sequences.

VII. Utility

The present invention relates to the cloning of a gene expressed at very high levels in ripening fruit, e.g., raspberries. The gene isolated from raspberry was designated dru1 and encodes a protein with a molecular weight of 17 kd. Analysis of protein expression in raspberry drupelets indicates dru1 comprises at least 23% of the total protein. Combined with dru2, an apparently similar 15kd protein expressed at even higher levels, these two proteins comprise at least 65% of the protein in raspberry drupelets. This is an unusually high level of gene expression for any plant tissue other than seed storage proteins.

Experiments performed in support of the present invention demonstrate that the gene expression patterns of the mature protein and mRNA encoded by the dru1 gene are strictly regulated to the receptacles and drupelets of ripening raspberries. Accordingly, use of the dru1 promoter allows the targeting of foreign gene expression to fruit tissues (i.e., when such foreign gene is placed under the control of the dru1 promoter). The dru2 gene and corresponding promoter regions may be characterized essentially as described herein for dru1.

dru1 can be cloned as described above employing N-terminal amino acid sequence information and corresponding degenerate PCR primers used in RT-PCR reactions to obtain a cDNA clone. Inverse PCR can be used to obtain a genomic clone of the gene including the dru1 promoter.

The dru1 gene represents an import discovery in the field of agricultural biotechnology from several standpoints. First, the dru1 promoter can be used to express any heterologous gene whose function would be enhanced or enabled by a high level, tissue specific promoter. Two examples of such genes have been described herein: the SAMase gene (for control of ethylene synthesis and therefore ripening control), and the PGIP gene (for fungal control, specifically gray mold or *Botrytis cinerea*). Other exemplary genes are described above.

Second, the use of this promoter cannot be considered limited to raspberries. The raspberry is essentially a miniature drupe fruit so it is likely that the dru1 promoter will function in other drupe fruits. The constructs and methods of the present invention are applicable to all higher plants including, but not limited to, the following: Berry-like fruits, for example, Vitis (grapes), Fragaria (strawberries), Rubus (raspberries, blackberries, loganberries), Ribes (currants and gooseberries), Vaccinium, (blueberries, bilberries, whortleberries, cranberries), Actinida (kiwifruit and Chinese gooseberry). Further, other drupe fruits, including, but not limited to, Malus (apple), Pyrus (pears), most members of the Prunus genera, sapota, mango, avocado, apricot, peaches, cherries, plums, and nectarines. Control of ethylene production via, for example, a dru1pro:SAMase chimera would be valuable in climacteric fruits (e.g., peaches and plums) which suffer from over-ripening in post-harvest distribution systems.

Further, the results described herein that the dru1 gene is expressed in receptacles makes it likely that the promoter will function in strawberries. The strawberry fruit is a swollen receptacle that is indistinguishable, from a botanical standpoint, from the raspberry receptacle. All drupe fruits (e.g., raspberries) and strawberries are members of the Rosacea genera thus making the dru1 promoter likely to function as a fruit specific promoter in heterologous species of this genera.

The present invention provides compositions and methods to regulate plant cell expression of any gene in a tissue and/or stage-specific manner. In one embodiment, the invention teaches the use of the dru1 tissue and stage-specific promoter whose expression is induced during fruit ripening.

In one embodiment, the promoters of the present invention can be used to regulate cellular production of ethylene. In this embodiment, a gene whose product results in a reduction of ethylene synthesis is operably linked to a dru1 promoter (creating a chimeric gene). When the chimeric gene is present in fruit cells, the result is fruit having a modified ripening phenotype relative to wild-type (non-transgenic) fruit.

Exemplary gene products that result in reduction of ethylene synthesis include, but are not limited to the following: S-adenosylmethionine hydrolase; 1-aminocyclopropane-1-carboxylate deaminase (Klee, et al., 1991; Sheehy, et al., 1991); the ACC synthase gene in an antisense or cosuppression configuration (Oeller, et al., 1991; Van der Straeten, et al., 1990); and the ACC oxidase gene in either an antisense or cosuppression configuration (Hamilton, et al., 1990; Holdsworth, et al., 1987). Cosuppression has been described by Jorgensen, et al., (1991, 1993), both herein incorporated by reference.

Other gene products that may be useful in the reduction of ethylene biosynthesis include catalytic antibodies and ribozyme molecules.

The present invention provides, in one aspect, nucleic acid constructs suitable for transforming plants with heterologous genes under the control of a dru1 promoter. In one embodiment, the plant is a fruit-bearing plant, and the heterologous gene is a gene effective to reduce ethylene biosynthesis in fruit from the plant.

Experiments performed in support of the present invention describe the construction of chimeric gene constructs containing the Adometase (or SAMase) gene, isolated from bacteriophage T3 (Ferro, et al., (1995), herein incorporated by reference; Hughes, et al., 1987).

The dru1 promoter may be employed in vector constructs used to produce transgenic plants, such as transgenic raspberries. For example, a vector engineered according to methods of the present invention containing the dru1 promoter connected to the AdoMetase gene (e.g. vector pAG-4032), may be used to produce transgenic raspberries, strawberries, peaches, plums and the like. The AdoMetase gene will be expressed in the fruit of these transgenic plants and will delay ripening. An advantage of the method of the present invention compared to other ripening inhibition approaches, namely antisense and/or cosuppression of ACC oxidase and ACC synthase, is a savings of time and resources involved in vector construction, since the same vector can be used to transform many different plant types.

Alternatively, dru1 promoter sequences may be isolated from the same type of plant that is to be transformed, and incorporated into the vector constructs used to perform the transformations. For example, a strawberry dru1 promoter may be connected to a heterologous gene, such as the AdoMetase gene, and used to transform strawberries.

The following examples illustrate, but in no way are intended to limit the present invention.

Materials and Methods

Oligonucleotides were synthesized by Operon Technologies, Inc., Alameda, Calif.

Generally, the nomenclature and laboratory procedures with respect to standard recombinant DNA technology can be found in Sambrook, et al., (1989); Wang, et al., (1989); Kawasaki, et al. (1989), and in Gelvin and Schilperoot (1988). Other general references are provided throughout this document. The procedures therein are known in the art and are only provided for convenient reference.

VIII. EXAMPLES

Example 1

Raspberry Drupelet Protein Characterization and Purification

A. Protein Lysate Preparation and Gel Electrophoresis

Using a mortar and pestle containing liquid nitrogen, a raspberry protein sample was prepared by grinding the frozen drupes of one whole berry into a fine powder. Sample buffer (0.05 M Tris, pH 6.8, 1% SDS, 5% beta-mercaptoethanol, 10% glycerol; Laemelli, 1970) was added (900 µls) to the tissue and the sample mixed by vortexing. The sample was heated for 10 minutes at 90–95° C. and centrifuged at 14K rpm, 4° C. for 10 minutes. The supernatant was removed from the insoluble debris pellet and stored at −20° C.

Drupelet proteins were analyzed by sodium dodecyl sulfate polyacrylamide gel electrophoresis (SDS PAGE) combined with coomassie blue staining using standard procedures for these steps. A coomassie blue-stained SDS polyacrylamide gel of soluble drupelet proteins is shown in FIG. 1. In the figure: lane 1, molecular weight markers (BioRad, Richmond, Calif.), lanes 2, 3 and 5 each contain 9 µg of raspberry drupelet protein lysate prepared separately from individual fruit. Lane 4 had a higher amount of lysate.

Two highly abundant proteins were observed at approximately 17 and 15 kd and were named drupe1 and drupe2, respectively. In FIG. 1 these two proteins are indicated by arrows. Scanning densitometry analysis of this gel indicated drupe1 and drupe2 comprise approximately 23 and 37%, respectively, of the total soluble protein in raspberry drupelets. As a result of this determination, a direct western blot approach to purification and sequencing of the protein was taken.

B. Protein Blot For Sequencing

A protein blot (Applied Biosystems, Inc. User Bulletin Number 58; Ausubel, et al., 1992) was prepared using the raspberry protein lysate described above. Varying amounts of raspberry protein lysate (12–36 µg/well) were loaded on a 10 well 18% SDS-PAGE minigel (1.5 mm thick) with 4.5% stacker and electrophoresed at 100 volts in 25 mM Tris, 192 mM glycine, 0.1% SDS buffer for 2–2.5 hours.

Proteins were transbiotted onto Applied BioSystem's "PROBLOTT" polyvinylidene difluoride (PVDF) membrane in a 25 mM Tris, 192 mM glycine, 10% methanol buffer at 90 volts for 2 hours at 4° C. After protein transfer, the blot was Coomassie blue stained and the 15 and 17 kilodalton (kd) protein bands were located on the blot and cut out. N-terminal sequencing of the proteins was carried out at the W. M. Keck Foundation, Biotechnology Resource Laboratory in New Haven, Conn.

The drupe1 sample yielded a thirty amino acid N-terminal sequence. The drupe2 sample did not yield useful sequence information likely due to a blocked amino terminus. The amino terminal drupe1 sequence is presented as SEQ ID NO:1. This 30 amino acid drupe1 sequence was compared to the protein database using BLAST searching; no significant matches were found indicating that drupe1 is a novel protein.

Example 2

Recovering a cDNA Clone Corresponding to the Drupe1 Protein

A. Drupelet Total RNA Preparation

RNA was extracted from mature green raspberry drupelets. Four mature green raspberry fruit, which had been picked in season and stored at −80° C., were used to extract RNA. The estimated weight of the drupelets was 12 grams. In a cold mortar, which contained liquid nitrogen, the whole berries were fractured by tapping them with a pestle. The drupelets were separated from the receptacles. The receptacles were removed from the mortar and discarded. The drupelets were ground to a powder in the mortar, adding liquid nitrogen as necessary to keep the tissue frozen. The seeds were purposefully left intact. Homogenization buffer, 2 ml/gram of tissue, was used to extract the RNA. [Homogenization buffer: 200 mM Tris-HCl pH 8.5, 300 mM LiCl, 10 mM $Na_2EDTA$, 1% (w/v) sodium deoxycholate, 1.5% (w/v) sodium dodecyl sulfate (SDS), 8.5% (w/v) insoluble polyvinylpolypyrrollidone (PVPP), 1% (v/v) NP-40, 1 mM aurintricarboxylic acid (ATA), 5 mM thiourea, and 10 mM dithiothreitol (DTT); the last three components were added after autoclaving].

The frozen powdered drupelet tissue was added to the buffer in 3 to 5 portions, vortexing between additions until all tissue was moistened. The tissue plus buffer solution (referred to herein as the pulp) was diluted 1:1 with sterile water and 0.75 volumes of homogenization buffer were added to the diluted pulp. The sample was incubated at 65° C. for 10 to 15 minutes, followed by centrifugation in a swinging bucket rotor at 9000 g for 15 minutes at 4° C. The supernatant was transferred to a clean tube. Cesium chloride (CsCl) was added to the supernatant at 0.2 g/ml. The sample was mixed until the CsCl dissolved.

A 4 ml cushion was dispensed into a Beckman 1×3.5 inch polyallomer ultracentrifuge tube (cushion: 5.7 M CsCl, 10 mM Tris-HCl, pH 8.0, 1 mM $Na_2EDTA$, pH 8). The sample was gently layered on top of the cushion. The sample was spun in a Beckman L8-80M ultracentrifuge with a SW 28 rotor at 23,000 rpm at 20° C. for 20 hours. After removing the sample from the ultracentrifuge the supernatant was pulled off the sample by using a drawn Pasteur pipette attached to an aspirator. A clear lens-like pellet was visible in the bottom of the tube.

The pellet was dissolved in 500 μl SSTE and transferred to a microfuge tube (SSTE: 0.8 M NaCl, 0.4% SDS, 10 mM Tris-HCl, pH 8.0 and 1 mM $Na_2EDTA$, pH 8). The sample was extracted twice with an equal volume of chloroform:isoamyl alcohol (24:1). To precipitate the RNA, 2.5 volumes ethanol were added to the aqueous phase. The sample was collected by centrifugation, washed two times with 75% ethanol and resuspended in 100 μl TE. The yield was 1.6 mg. The RNA was re-precipitated with ⅕ volume 3 M Sodium Acetate and 3 volumes ethanol for storage at −20 ° C.

B. Drupelet mRNA Preparation

The isolation of mRNA from mature green raspberry drupelet total RNA was performed using the "STRAIGHT A'S" mRNA isolation system (Novagen, Madison, Wis.) according to the manufacturer's instructions. mRNA was isolated from the 1.6 mg of total RNA extracted from mature green raspberry drupelets described above. The yield of mRNA from this procedure was 6.6 μg.

C. Making cDNA From Green Raspberry Drupelet mRNA

The mRNA from mature green raspberry drupelet RNA was used as the template for cDNA synthesis. The primer for the cDNA reactions was dTRANDOM (SEQ ID NO:2; synthesized by Operon Technologies, Inc., Alameda, Calif.). The oligo(dT) region hybridized to the poly(A) region (corresponding to SEQ ID NO:23, as shown in the top portion of FIG. 2A) of the mRNA pool. The other 15 nucleotides created a 5' overhang that was used to facilitate PCR amplification at a later step in the cloning process.

The following reaction mixture was assembled for the cDNA synthesis reaction: $H_2O$, 10.2 μl; 250 ng mRNA, 0.8 μl; 5× BRL RT buffer (BRL, Bethesda, Md.), 4.0 μL; 100 mM DTT (dithiothreitol—BRL, Bethesda, Md.), 0.2 μl; "RNAguard" (23.4 U/μl; an RNase inhibitor from Pharmacia, Piscataway, N.J.), 0.5 μl; dNTP's (2.5 mM each), 2.0 μl; 50 μM primer, 1.0 μl; [$^{32}P$]dCTP (3000 Ci/mmol; DuPont/NEN, Boston, Mass.), 1.0 μl; and AMVreverse-transcriptase (38 U/μl; Life Sciences, Inc., St. Petersburg, Fla.), 0.3 μl. The cDNA reaction was performed by combining mRNA and water for the reaction and heating to 65° C. for 3 minutes. The mixture was cooled on ice and microfuged (to collect condensation). The remaining reaction components were then added.

After incubating at 42° C. for 1 hour the cDNA reactions were moved to ice and stored at 4° C. prior to their use in PCR reactions. The preparation of cDNA from mRNA is illustrated in the top portion of FIG. 2A. A portion of the 3' end of the first cDNA strand is shown in the second set of reactions in FIG. 2A, the sequence of which is presented herein as SEQ ID NO:24.

Example 3

PCR Amplification and Cloning of the cDNA Dru1 Fragment

A degenerate PCR primer, Drupe20, was designed for the 5' end of the cDNA based on the reverse translation of the dru1 protein sequence. A section of the known amino acid sequence of dru1 (SEQ ID NO:3) was chosen for its proximity to the amino terminus and for the relatively low level of degeneracy in its reverse-translated sequence (SEQ ID NO:4; Drupe20). The Drupe20primer (i) is the 512-fold degenerate nucleotide sequence corresponding to the amino acid sequence presented as SEQ ID NO:3, and (ii) was used as the 3'-primer. The product from the first round of PCR amplification is illustrated in FIG. 2A (second set of reactions), where a portion of the sequence at the 3' end of the product corresponds to SEQ ID NO:25 (which is also the complement of SEQ ID NO:2).

The 5' PCR primer (DrupeRAN18, SEQ ID NO:5, corresponding to the cDNA primer, dTRANDOM) was designed for the 3' end. The product from the second round of PCR amplification is shown in FIG. 2A (third set of reactions), where a portion of the sequence corresponding to the 3' end of the product is presented herein as SEQ ID NO:26 (which is also the complement of SEQ ID NO:4). Polymerase chain reaction (PCR; Perkin-Elmer Cetus, Norwalk, Conn.; Mullis, 1987; Mullis, et al., 1987, was performed following the manufacturer's procedure using "AMPLITAQ" (Perkin Elmer Cetus), PCR buffer II (50.0 mM KCl, 10 mM Tris-HCl, pH 8.3), 2 mM $MgCl_2$, 0.2 mM of each dNTP, mature green drupelet cDNA and Drupe20and DrupeRAN18 primers under the following conditions:

1 cycle at 95° C., 1 minute, 35 cycles at 95° C. for 1 minute, 42° C. for 1 minute and 72° C. for 1 minute, 1 cycle at 72° C. for 5 minutes, and cooling to 5° C.

There were two major products of the amplification reaction: a predominant product of approximately 700 bp and a less abundant product of approximately 500 bp. The 700 bp band was isolated from a 1% "SEAPLAQUE" agarose gel using β-agarose (NEB, Beverly, Mass.) according to the supplier's instructions. This fragment was then ligated to the vector pCRII, the TA cloning vector from Invitrogen (San Diego, Calif.), following the manufacturer's instructions.

The cDNA clones of the dru1 gene were identified by screening plasmid miniprep DNA prepared from 1.6 ml of culture using the alkaline lysis method (Ausubel, et al., 1992). The cDNA product is illustrated schematically in the bottom portion of FIG. 2A, where SEQ ID NO:27 corresponds to a portion of the 3' end which includes the polyA tail. The double-stranded DNA was sequenced by the dideoxy chain-termination method using the "SEQUENASE" ver.2 enzyme and kit components (United States Biochemical, Cleveland, Ohio) and [α-$^{35}$S]-dATP (DuPont/NEN). The reactions were primed with the M13 universal forward and reverse primers (NEB, Beverly, Mass.). Sequencing reactions were resolved on an acrylamide gel ("LONG RANGER GEL,"FMC, Rockland, Me.) and bands detected by autoradiography.

The sequence was read from the autoradiograph and analyzed for its homology with the reverse translated N-terminal protein sequence from drupe1. The actual DNA sequence was determined, as opposed to the degenerate DNA sequence obtained through reverse translation of the protein sequence. In addition, the correlation between the cDNA and the remainder of the N-terminal protein sequence was confirmed. A clone (designated pAG-301) was selected, following these criteria, for further characterization. The nucleic acid sequence of the dru1 cDNA insert of pAG-301 is presented as SEQ ID NO:10.

The entire dru1 cloning procedure from cDNA synthesis to inverse PCR of a genomic copy of the gene is shown schematically in FIGS. 2A and 2B.

Example 4

Recovering the Genomic DNA Fragment Corresponding to the dru1 cDNA

The "CTAB" (hexadecyl-trimethyl-ammonium bromide) method (Doyle and Doyle, 1990) was used to extract DNA from raspberry leaves. PCR primers (DruGen5', SEQ ID NO:6; DruGen3', SEQ ID NO:7) were designed based upon the complete dru1 cDNA sequence. "OLIGO," a multi-functional program from National Biosciences, Inc. (Plymouth, Minn.), was used to facilitate design of the primers. PCR was performed following the manufacturer's procedure using "AMPLITAQ" (Perkin-Elmer Cetus), PCR buffer (50.0 mM KCl, 10 mM Tris-HCl pH 8.3, and 1.5 mM MgCl$_2$), 0.2 mM of each dNTP, raspberry genomic DNA and DruGen5' and DruGen3' primers under the following ("HOT START") conditions:

1 cycle of 97° C. for 5 minutes, after which the "AMPLITAQ" was added, 2 cycles of 97° C. for 1 minute, 52° C. for 1 minute and 72° C. for 1 minute, 25 cycles of 94° C. for 1 minute, 52° C. for 1 minute and 72° C. for 1 minute, 1 cycle of 72° C. for 5 minutes, and cooling to 5° C.

This amplification reaction produced 3 major products: a predominant product of 710 bp and 2 less abundant products of 690 and 625 bp. The PCR reaction products were then ligated to the vector pCRII, the TA cloning vector from Invitrogen (San Diego, Calif.), following the manufacturer's instructions. A clone was selected with a 710 bp insert and designated pAG-302.

Plasmid DNA of pAG-302 was prepared from 1.6 ml of culture using the alkaline lysis method (Ausubel, et al., 1992) and sequenced by the dideoxy chain-termination method using "SEQUENASE" ver.2 enzyme and kit components (USB, Cleveland, Ohio) and [α-35S]-dATP (DuPont/NEN). The sequencing reactions were primed with the M13 universal forward and reverse primers (NEB, Beverly, Mass.). Further sequencing reactions were primed with 2 additional internal primers. Sequencing reactions were resolved on an acrylamide gel and detected through autoradiography.

The sequence of the dru1 genomic DNA insert in pAG-302 is presented as SEQ ID NO:11.

The sequence of the clone demonstrated that a genomic DNA fragment corresponding to the dru1 cDNA had been isolated.

Example 5

Recovering the 5' Flanking Region of the dru1 Genomic DNA Through Inverse PCR

Inverse PCR primers (designated DruInvUp, SEQ ID NO:8, and DruInvLow, SEQ ID NO:9) were designed based upon the genomic DNA sequence and optimized using OLIGO. Genomic raspberry DNA was digested with restriction enzyme NsiI. NsiI was chosen because, based on the cDNA sequence, NsiI was known to cut in the 3'-untranslated region of the gene. A small portion of the NsiI digested DNA was run on an analytical agarose gel and a Southern transfer was performed (Ausubel, et al., 1992).

The Southern blot was probed with the cDNA fragment contained in pAG-302. The probe identified a NsiI fragment of about 2–2.3 kb: this fragment hybridized strongly with the genomic clone. A second, smaller fragment hybridized to the probe as well but hybridized weakly with the genomic clone.

The remaining NsiI-digested raspberry DNA was electrophoresed on a 1% "SEAPLAQUE" agarose gel (FMC, Rockland, Me.). Using a BstEII lambda size standard as a guide, the digested DNA in the range of 2–2.3 kb was excised from the gel. The DNA was purified using β-agarose (NEB, Beverly, Mass.) following the manufacturer's instructions. The DNA was self ligated at a relatively dilute concentration (1 μg/ml) to bias the formation of circular ligation reaction products (Ochman, et al., 1990).

Inverse PCR was subsequently performed on the self-ligated, NsiI-digested, size-selected, genomic raspberry DNA. "AMPLITAQ" from Perkin Elmer Cetus was used to amplify the DNA. The manufacturer's procedure was followed using PCR buffer, 0.2 mM of each dNTP, raspberry genomic DNA (prepared as described herein), and DruInvUp and DruInvLow primers. The following ("HOT START") reaction conditions were employed:

One cycle at 97° C. for 5 minutes, after which the "AMPLITAQ" was added, 2 cycles at 97° C. for 1 minute, 58° C. for 1 minute and 72° C. for 1 minute, 25 cycles at 94° C. for 1 minute, 58° C. for 1 minute and 72° C. for 1 minute, 1 cycle at 72° C. for 5 minutes, and cooling to 5° C.

This reaction produced 2 major amplification products, one of 1.8 kb and one of 900 bp. The 1.8 kb band was isolated from a 1% "SEAPLAQUE" agarose gel using β-agarose. This fragment was ligated to pCRII to give rise to pAG-310.

The pAG-310 insert was sequenced in its entirety (SEQ ID NO:12) and the dru1 insert sequence was found to be identical to the cDNA clone (SEQ ID NO:10) and the genomic clone (SEQ ID NO:11) in the regions where sequence was shared. The normal elements of plant genes and their regulatory components were identified (FIGS. 3A and 3B) including a CAAT box, TATA box, ATG start codon, two exons, an intron, splicing sites, a stop codon and poly-adenylation sites.

Figure 4:
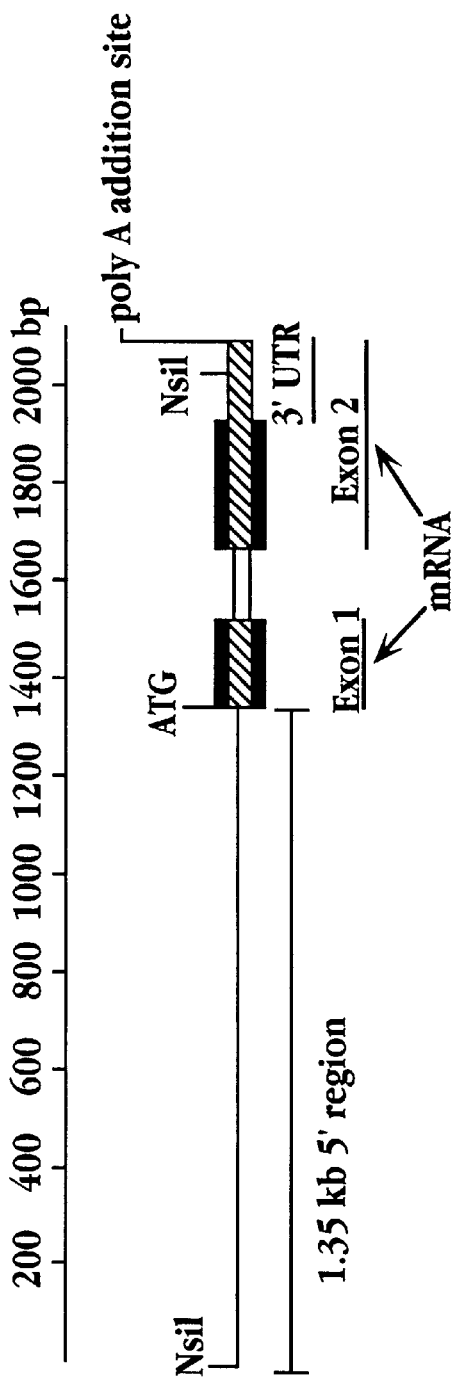
FIG. 4 presents a schematic representation of the gene organization and protein structure of dru1.
Figure 5:
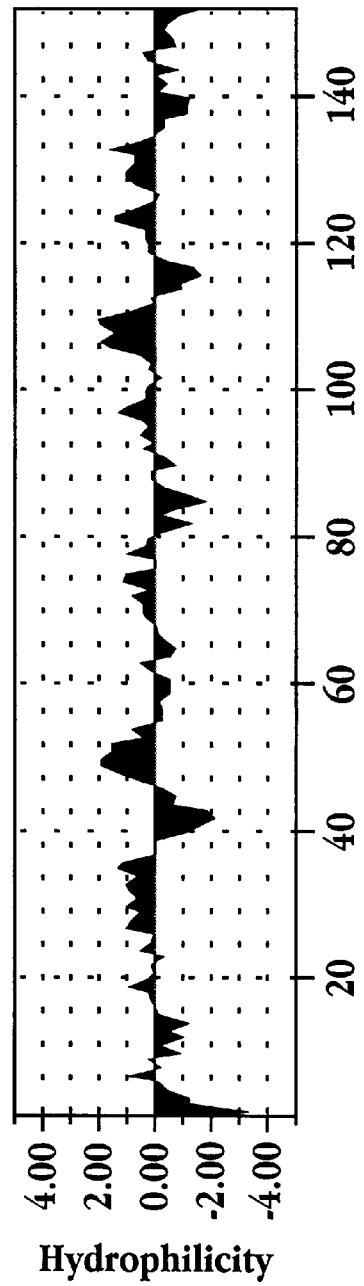
FIG. 5 presents a Kyte-Doolittle hydrophilicity plot of the coding sequence of dru1. In the figure, the hydrophilicity window size=7.

The gene organization and protein structure of dru1 is schematically displayed in FIG. 4. The gene encodes a protein having the predicted amino acid sequence presented as SEQ ID NO:13. The predicted protein has a calculated molecular weight of 17,087.64 and an estimated pI of 4.80. A Kyte-Doolittle hydrophobicity plot of the dru1 protein is presented as FIG. 5.

Example 6

Characterization of dru1 Gene Expression

A. RNA Dot Blots

Figure 6:
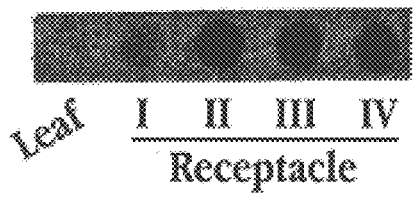
FIG. 6 shows the results of RNA dot blot analysis of dru1 RNA expression in raspberry leaf and receptacle. RNA was isolated from green, mature green, breaker & orange/ripe raspberries (corresponding to stages I, II, III, IV, respectively).

RNA dot blots were prepared using 5 μg of total raspberry leaf RNA and 5 μg each of total receptacle RNA from green, mature green, breaker & orange/ripe raspberries (corresponding to stages I, II, III, IV, respectively, in FIG. 6). The blots were probed with the dru1 cDNA fragment, labeled with [32-P]dCTP (>3000 Ci/mmole) by the random primed method (Boehringer Mannheim Biochemicals, Random Primed reaction kit, Indianapolis, Ind.).

The blots were allowed to hybridize overnight at 45° C. in "HYBRISOL I" (Oncor, Gaithersburg, Md.). A probe concentration of $1.2 \times 10^7$ DPM/ml was used. The blot was washed after the overnight hybridization with a final wash using 0.1× SSC at 42° C. for 1 hour. The hybridizing probe was detected through standard autoradiographic methods. The exposure of the blot to film was for 4 hours and 10 minutes with an intensifying screen at −80° C.

The results of this analysis are shown in FIG. 6. In the figure the RNA dots are, respectively from left to right, leaf RNA and receptacle RNA from green (FIG. 6, "I"), mature green (FIG. 6, "II"), breaker (FIG. 6, "III") and orange/ripe raspberries (FIG. 6, "IV").

B. Further RNA Hybridization Analysis

A plant RNA extraction method (Chang, et al., 1993) was used for receptacles and leaves. The raspberry drupelet RNA extraction method described above was used for the drupelets and strawberry fruit.

A Northern blot was prepared using 5 μg/lane of each sample RNA. The RNA samples were as follows: raspberry leaf (FIG. 7, lane 1), mature green raspberry receptacles (FIG. 7, lane 2), orange/ripe raspberry receptacles (FIG. 7, lane 3), mature green raspberry drupelets (FIG. 7, lane 4), and orange/ripe raspberry drupelets (FIG. 7, lane 5).

The blot was probed with the dru1 cDNA fragment, labeled with [$^{32}$P]dCTP (>3000 Ci/mmole) by random primed reactions. Hybridization was carried out overnight at 45° C. in "HYBRISOL I" (Oncor, Gaithersburg, Md.). A probe concentration of $4.2 \times 10^6$ DPM/ml was used. The blot was washed after the overnight hybridization with a final wash using 0.1× SSC at 50° C. for 30 minutes. The hybridizing probe was detected through standard autoradiographic methods. The exposure of the blot to film was for 1 hour at room temperature without an intensifying screen.

Figure 7:
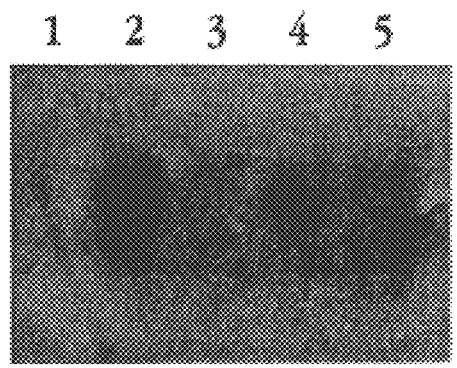
FIG. 7 shows the results of a RNA hybridization study evaluating the expression of dru1 RNA in raspberry leaf and fruit.

The results of this analysis are presented in FIG. 7 and support a stage specific expression pattern in drupelets.

C. Protein Expression Analysis

Protein lysates were prepared (as described in Example 1) from raspberry drupelets at various stages of ripening. The lysates were size-fractionated by PAGE and the gel stained with Coomaise blue (50% MeOH, 10 mM Tris-HCl pH 8.3, 1.5 mM MgCl2). The results of this work are presented in FIG. 8. In the figure the lysates in the lanes were as follows: lane 1, green drupelet; lane 2, mature green drupelet; lane 3, breaker drupelet; lane 4, orange drupelet; and lane 5, ripe drupelet. The results of this analysis supports a stage specific expression pattern in drupelets.

Example 7

Chimeric Genes Containing the dru1 Promoter

A. Construction of a dru1pro:SAMase Binary Vector

A fragment containing the Dru1 promoter was PCR amplified from pAG-310 using primers DruPro5'RI (SEQ ID NO:14) and DruPro3'(SEQ ID NO:15) and standard PCR reaction conditions. The amplification reaction produced a 1.3 kb fragment product. This fragment was digested to completion with EcoRI and NcoI. The digested fragment was ligated into pAG-112, a pUC vector carrying an AdoMetase encoding gene (Ferro, et al., 1995) with a nos terminator. The resulting plasmid was designated pAG-119.

pAG-119 plasmid DNA was digested to completion with SmaI and HindIII. A 2.1 kb fragment containing Dru1pro/SAM-Kozak/Nos terminator was recovered from 1% "SEAPLAQUE" agarose using β-agarose. pAG-4000 was obtained from pPZP-200 (Hajdukiewicz, et al., 1994) by inserting a CMVV/nptII/G7 terminator gene cassette into the multiple cloning site of pPZP-200. The CMVV (Cassava mottle vein virus) promoter was obtained from Scripps Research Institute, La Jolla, Calif.). pAG-4000 was digested with SmaI and HindIII and ligated to the 2.1 kb pAG-119 fragment to form vector pAG-4032. The details of this construction are described schematically in FIG. 9.

The complete nucleotide sequence of the dru1 promoter-:SAMase chimeric gene is presented as SEQ ID NO:16. The predicted amino acid coding sequence is presented as SEQ ID NO:17.

B. Construction of a dru1pro:PGIP Binary Vector

The PGIP gene (Toubart, et al., 1992) and its 3' untranslated region (UTR) was PCR amplified from pAD-16 (Toubart, et al., 1992) using the primers PGIPNco5' (SEQ ID NO:18) and PGIPPst3' (SEQ ID NO:19). The amplification reaction produced a product of 1.8 kb. This 1.8 kb fragment included a portion of the cloning vector. The fragment was digested with NcoI and PstI to completion resulting in a 1290 bp fragment which no longer contained portions of the cloning vector.

pAG-119 (see above) was prepared by digestion to completion with NcoI and PstI. This removed the SamK portion of the plasmid. The remaining portion of the plasmid was then ligated to the PGIP-containing fragment described above. This new plasmid was designated pAG-129.

pAG-129 was digested to completion with XbaI and PvuII (a restriction enzyme whose cleavage results in blunt ends). The 2.87 kb fragment containing Dru1pro/PGIP/Nos terminator was recovered from 1% "SEAPLAQUE" agarose by using β-agarose. The vector pAG-4033 was prepared by digestion to completion with XbaI and SmaI (a restriction enzyme whose cleavage results in blunt ends). This digestion removed the Dru1pro/SAM-Kozak/Nos terminator portion of the plasmid. The remaining portion of the plasmid was then ligated to the Dru1pro/PGIP/Nos terminator fragment described above. This new plasmid was named pAG-4033 and its construction is described schematically in FIG. 10.

The complete nucleotide sequence of the dru1 promoter-:PGIP chimeric gene is presented as SEQ ID NO:20. The predicted amino acid coding sequence is presented as SEQ ID NO:21.

Example 8

Southern Blot Analysis of dru1 Homologues in Several Species of Plants

A Southern blot analysis is conducted to determine if sequences homologous to the raspberry dru1 gene are present in other plant species. The blot consists of HindIII digests of six genomic plant DNAs, for example, tomato, raspberry, strawberry, plum, cherry and peach, along with size standards. Probes can be constructed using dru1 coding sequence-specific primers and polymerase chain reaction (PCR; Mullis, 1987; Mullis, et al., 1987). Alternatively, the 700 base pair insert from pAG-301 (SEQ ID NO:10) is isolated by digestion with EcoRI followed by size fractionation. The DNA fragment is then radioactively-labeled using the Bohringer Mannheim Biochemical (Indianapolis, Ind.) "RANDOM PRIMED DNA LABELING" kit. The blot is hybridized with the dru1-specific probe following standard methods (Maniatis, et al., 1982). Exemplary hybridization conditions are as follows: the blot is hybridized overnight at 45° C. with the dru1 probe in "HYBRISOL I" hybridization cocktail (Oncor, Gaithersburg, Md.). The final (most stringent) wash is 0.1% SSC, 0.1% SDS for 30 minutes at room temperature (22° C.).

An autoradiograph of the blot is used to identify plant species to whose genomic DNA the dru1 probe can hybridize.

Example 9

Isolation of DNA Fragments Homologous to dru1 from a Strawberry Genomic Library

A. Screening of the Library

A custom strawberry genomic library in lambda GEM-11 is obtained from Novagen (Madison, Wis.) and screened by standard methods with the dru1 gene probe described above. Lambda clones which hybridized to the probe are identified. The clones are purified by 3 rounds of plaque purification. Hybridization-positive clones are selected for further analysis.

B. Analysis of a Positive Clone

A clone of interest is digested with several enzymes (e.g., ApaI, BamHI, EcoRI, HindIII, NcoI, SacI, and SalI), run on a gel, and transferred to a "SUREBLOT" nylon membrane (Oncor, Gaithersburg, Md.). The blot is hybridized overnight at 45° C. with the dru1 probe in "HYBRISOL I" hybridization cocktail (Oncor, Gaithersburg, Md.). The final (most stringent) wash is 0.1% SSC, 0.1% SDS for 30 minutes at room temperature (22° C.).

A hybridization-positive fragment is subcloned into pGEM5Zf(+) (Promega, Madison, Wis.) and further characterized. The nucleic acid sequence of the insert is determined and the amino acid sequence predicted from the nucleic acid sequence. These sequences are then compared to the raspberry dru1 nucleic acid and protein sequences.

Additional strawberry dru1 gene sequences are obtained by further hybridization screening of strawberry genomic library clones.

While the invention has been described with reference to specific methods and embodiments, it will be appreciated that various modifications and changes may be made without departing from the invention.

It is claimed:

1. A plant transformed with a chimeric gene comprising a dru1 promoter operably linked to a heterologous DNA coding sequence.

2. The plant of claim 1, where said promoter is a raspberry dru1 promoter.

3. The plant of claim 1, where said heterologous DNA sequence encodes a product conferring fungal resistance to plant cells.

4. The plant of claim 1, wherein said promoter (i) is encoded by a DNA molecule having a sequence which hybridizes with a DNA molecule having the sequence presented as SEQ ID NO:22, under conditions wherein hybridization is conducted at 43° C. in 50% formamide, 6× SSC, 5× Denhardt's solution, 0.5% SDS and 100 ?g/ml denatured carrier DNA followed by washing two times in 2× SSPE and 0.5% SDS at room temperature and two additional times in 0.1× SSPE and 0.5% SDS at 43° C., and (ii) is a fruit-ripening induced or fruit-specific promoter.

5. The plant of claim 1, wherein said promoter is a fruit-ripening induced or fruit-specific promoter from a plant dru1 gene whose coding sequence will hybridize with a DNA molecule having the sequence presented as SEQ ID NO:12, under conditions wherein hybridization is conducted at 43° C. in 50% formamide, 6× SSC, 5× Denhardt's solution, 0.5% SDS and 100?g/ml denatured carrier DNA followed by washing two times in 2× SSPE and 0.5SDS at room temperature and two additional times in 0.1× SSPE and 0.5% SDS at 43°.

6. The plant of claim 1, where said plant is a fruit-bearing plant.

7. A fruit produced by the plant of claim 6.

8. A fruit of claim 7, selected from the group consisting of grape, strawberry, raspberry, blackberry, plum, cherry, peach, blueberry, pear, apple and cranberry.

9. A seed produced by the plant of claim 6.

10. The plant of claim 1, where said heterologous DNA coding sequence comprises a ripening modification gene.

11. The plant of claim 10, where said heterologous DNA sequence encodes a product selected from the group consisting of S-adenosylmethionine hydrolase, aminocyclopropane-1-carboxylic acid (ACC) deaminase, ACC oxidase antisense molecule, ACC synthase antisense molecule, ACC oxidase cosuppression molecule, and ACC synthase cosuppression molecule.

12. A fruit containing a chimeric gene comprising a dru1 promoter operably linked to a heterologous DNA coding sequence.

13. A seed transformed with a chimeric gene comprising a dru1 promoter operably linked to a heterologous DNA coding sequence.

14. A method for providing fruit-specific or ripening-induced expression of a heterologous DNA coding sequence in fruit of a fruit-bearing plant, comprising:

(i) transforming a plant cell of a fruit-bearing plant with a chimeric gene comprising a dru1 promoter operably linked to a heterologous DNA coding sequence, to produce a transformed plant cell, and (ii) growing the transformed plant cell to produce a transgenic fruit-bearing plant, where said promoter is effective to induce expression of said DNA coding sequence in fruit of said plant at the ripening stage of fruit development.

15. The method of claim 14, where said plant cell is selected from the group consisting of grape, strawberry, raspberry, blackberry, plum, cherry, peach, blueberry, pear, apple and cranberry.

16. A method for producing a transgenic plant, comprising:

transforming a plant cell with a chimeric gene comprising a dru1 promoter operably linked to a heterologous DNA coding sequence to produce a transformed plant cell, and growing the transformed plant cell to produce a transgenic plant.

* * * * *